(12) United States Patent
Bowden et al.

(10) Patent No.: US 6,849,728 B1
(45) Date of Patent: Feb. 1, 2005

(54) GLUT10: A GLUCOSE TRANSPORTER IN THE TYPE 2 DIABETES LINKED REGION OF CHROMOSOME 20Q12-13.1

(75) Inventors: David W. Bowden, Winston-Salem, NC (US); Paul A. Dawson, Winston-Salem, NC (US); Sallyanne C. Fossey, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 09/652,292

(22) Filed: Aug. 31, 2000

(51) Int. Cl.[7] .......................... C12N 5/10; C12N 15/12; C12N 15/63
(52) U.S. Cl. ................... 536/23.5; 435/69.1; 435/71.1; 435/71.2; 435/325; 435/320.1; 435/252.3; 435/254.11; 435/471
(58) Field of Search .............................. 536/23.5, 23.1, 536/24.3; 435/252.3, 254.11, 320.1, 325, 471, 71.1, 71.2, 69.1, 7.1, 7.2, 70.1, 325.1; 330/330, 350

(56) References Cited

PUBLICATIONS

Marra, M et al, Uc76f10.x1 Sugano mouse liver mlia Mus musculus cDNA clone IMAGE:1431595', mRNA sequence, EST Database, Accession No. AI042706, Jul. 1, 1998.*

Ramsey, H, Human Sequence from clone RP1–28H20 on chromosome 20q13.1, GenEmbl database, Accession No. AL031055, Arp. 19, 2001.*

* cited by examiner

*Primary Examiner*—Prema Mertz
(74) *Attorney, Agent, or Firm*—Myers Bigel Sibley & Sajovec, P.A.

(57) ABSTRACT

GLUT 10 is an insulin-responsive glucose transporter gene located in the type 2 diabetes linked region of chromosome 20Q12-13.3. Isolated nucleic acids encoding the GLUT 10 glucose transporter, the encoded protein, antibodies that bind the protein, and methods of use are described herein.

6 Claims, 9 Drawing Sheets

Fig. 1

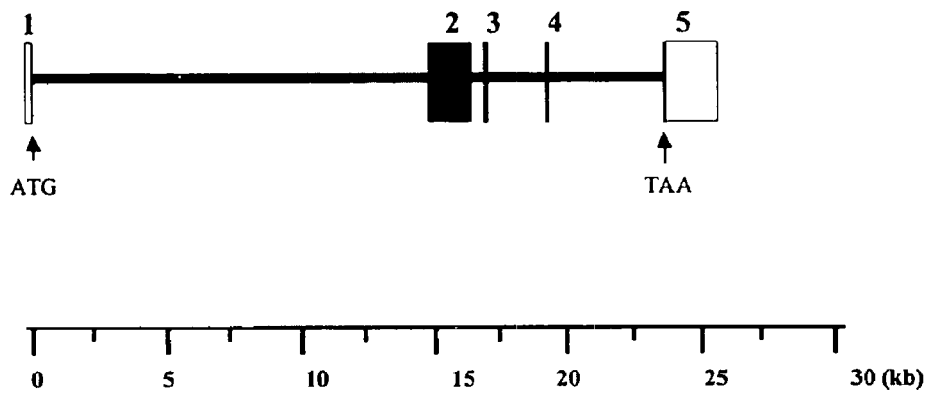

| EXON | EXON SIZE | 3' SPLICE ACCEPTOR | 5' SPLICE DONOR | INTRON SIZE |
|---|---|---|---|---|
| 1 | 254 | | TCGCCATG G / gtaagtc<br>Met G<br>1 2 | 15300 |
| 2 | 1284 | tttttag / GC CAC TCC<br>ly His Ser<br>2 3 4 | GGG CCA G / gtaagtg<br>Gly Pro V<br>428 429 4 | 538 |
| 3 | 123 | accctag / TG ACC TGG<br>al Thr Trp<br>30 431 432 | CTC ATT G / gtgagtc<br>Leu Ile G<br>469 470 4 | 2365 |
| 4 | 135 | tttccag / GC ACC ATC<br>ly Thr Ile<br>71 472 473 | AAG AGA CG / gtaggaa<br>Lys Arg Ar<br>514 515 516 | 4266 |
| 5 | 2849 | ctgacag / G TTC ACC<br>g Phe Thr<br>517 518 | AATAAAGAGTTTGTTATTAATTTGT(A)$_n$ | 3' UTR<br>2519 |

FIG. 1B

| EXON | EXON SIZE | 3' SPLICE ACCEPTOR (SEQ ID NO:_) | 5' SPLICE DONOR (SEQ ID NO:_) | INTRON SIZE |
|---|---|---|---|---|
| 1 | 254 | | TCGCCATG G / gtaagtc (29)<br>Met G<br>1 2 | 15300 |
| 2 | 1284 | tttttag / GC CAC TCC (30)<br>ly His Ser<br>2 3 4 | GGG CCA G / gtaagtc (31)<br>Gly Pro V<br>428 429 4 | 538 |
| 3 | 123 | accctag / TG ACC TGG (32)<br>al Thr Trp<br>30 431 432 | CTC ATT G / gtgagtc (33)<br>Leu Ile G<br>469 470 4 | 2365 |
| 4 | 135 | tttccag / GC ACC ATC (34)<br>ly Thr Ile<br>71 472 473 | AAG AGA CG / gtaggaa (35)<br>Lys Arg Ar<br>514 515 516 | 4266 |
| 5 | 2849 | ctgacag / G TTC ACC (36)<br>g Phe Thr<br>517 518 | AATAAAGAGTTTGTTATTAATTGT(A)$_N$<br>(37) | 3' UTR<br>2519 |

FIG. 7A

Fig. 3
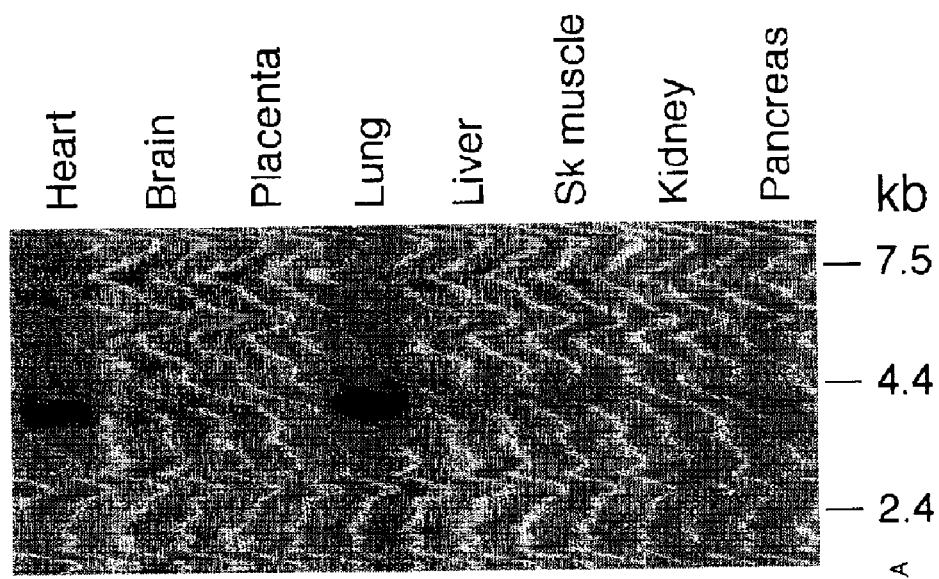
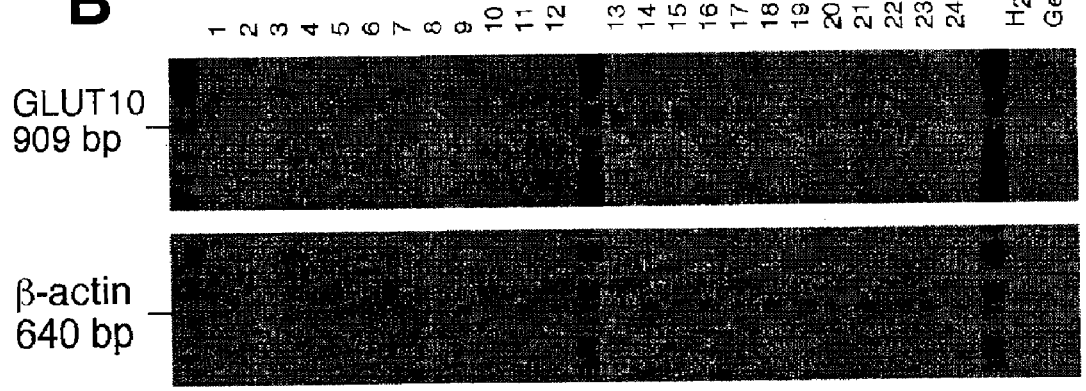
| | | |
|---|---|---|
| 1 Brain | 9 Muscle | 17 Ovary |
| 2 Heart | 10 Stomach | 18 Uterus |
| 3 Kidney | 11 Testis | 19 Prostate Gland |
| 4 Spleen | 12 Placenta | 20 Skin |
| 5 Liver | 13 Salivary Gland | 21 PBL |
| 6 Colon | 14 Thyroid Gland | 22 Bone Marrow |
| 7 Lung | 15 Adrenal Gland | 23 Fetal Brain |
| 8 Small intestine | 16 Pancreas | 24 Fetal Liver |

GLUT10: A GLUCOSE TRANSPORTER IN THE TYPE 2 DIABETES LINKED REGION OF CHROMOSOME 20Q12-13.1

STATEMENT OF FEDERAL SUPPORT

This invention was made possible with government support under grant numbers R01 DK41269, R01 DK53591, and R01 DK47987 from the National Institute of Health. The United States government has certain rights to this invention.

FIELD OF THE INVENTION

The present invention concerns the nucleic acid sequences encoding for glucose transporter proteins and the use of these proteins and nucleic acids in therapeutic, preventive, genetic counseling, and reagent screening applications.

BACKGROUND OF THE INVENTION

Glucose is an important source of energy for most living organisms. The movement of glucose across membranes is accomplished by two classes of transporters, the energy dependent $Na^+$-glucose cotransporters (Hediger, et al. (1989) *Proc. Nat. Acad. Sci. USA* 86, 5748–5752) and the facilitative glucose transporters. In humans, the facilitative glucose transporter family consists of at least six glucose transporters (Mueckler, et al. (1985) *Science* 229, 941–945; Fukumoto, et al. (1988) *Proc. Nat. Acad Sci. USA* 85, 5434–5438; Kayano, et al. (1988) *J. Biol. Chem.* 263, 15245–15248; Fukumoto, et al. (1989) *J. Biol. Chem* 264, 7776–7779; Ibberson, et al. (2000) *J. Biol. Chem.* 275, 4607–4612; Doege, et al. (2000) *J. Biol. Chem.* 275, 16275–80; Carayannopoulos, et al. (2000) *Proc. Natl. Acad. Sci. USA* 97, 7313–7318; Phay, et al. (2000) *Genomics* 66, 217–220) and a fructose transporter (Burant, et al. (1992) *J. Biol. Chem* 267, 14253–142; Davidson, et al. (1992) *Am. J. Physiol.* 262, C795–C800). These facilitative transporters regulate the movement of glucose between extra and intracellular spaces to maintain a constant supply of circulating glucose (Olson and Pessin. (1996) *Annu. Rev. Nutr.* 16, 235–256).

Defects in facilitative glucose transporters have been implicated in several metabolic disorders, including GLUT1 deficiency syndrome (Seidner, et al. (1998) *Nat. Genet.* 18, 188–91), Fanconi-Bickel Syndrome (Santer, et al. (1997) *Nat. Genet.* 17, 324–6) and Type 2 diabetes (Butler, et al. (1990) *Diabetes* 39, 1373–1380; Rothman et al. (1995) *Proc. Nat. Acad. Sci. USA* 92, 983–987; Cline, et al. (1999) *N. Engl. J. Med.* 341, 240–246). Type 2 diabetes is one of the most prevalent metabolic diseases, characterized by peripheral insulin resistance, impaired insulin production, and increased hepatic glucose production all contributing to hyperglycemia. Despite intensive investigation, the etiology of the disease remains unknown. The first glucose transporters identified (GLUT1–5) were extensively analyzed for mutations contributing to Type 2 diabetes, but to date no common causative mutation has been identified. However, several novel glucose transporters, GLUT8 and GLUT9 (Doege, et al. (2000) *J. Biol. Chem.* 275, 16275–80; Carayannopoulos, et al. (2000) *Proc. Natl. Acad. Sci. USA* 97, 7313–7318; Phay, et al. (2000) *Genomics* 66, 217–220), have recently been identified and additional glucose transporters may exist.

The results of several recent genetic linkage studies suggest that Type 2 diabetes in Caucasian patients is linked to the q12-q13.1 region of human chromosome 20 (Bowden, et al. (1997) *Diabetes* 46, 882–886; Ghosh, et al. (1999) *Proc. Natl. Acad. Sci.* USA 96, 2198–2203; Ji, et al. (1997) *Diabetes* 46, 876–881; Zouali, et al. (1997) *Hum. Mol. Genet.* 6, 1401–1408). Evidence of linkage disequilibrium with Type 2 diabetes has also been observed with alleles of two genetic markers within this linked region, adenosine deaminase (ADA) and D20S888, markers separated by approximately 6 cM (Price, et al. (1997) *Am. J. Hum. Genet.* 58 (suppl), A241).

The key metabolic role of glucose transport suggests that the identification of novel transporters may lead to new insights into the underlying biological processes of both glucose metabolism and Type 2 diabetes.

SUMMARY OF THE INVENTION

A first aspect of the present invention is an isolated nucleic acid encoding a GLUT 10 glucose transporter protein, such as an isolated nucleic acid selected from the group consisting of: (a) isolated nucleic acid having the sequence given herein as SEQ ID NO: 1; (b) isolated nucleic acids that hybridize to the complement of the sequence given herein as SEQ ID NO: 1 under stringent conditions and encode an insulin-responsive glucose transporter; and (c) isolated nucleic acids that differ from the sequences of (a) and (b) above due to the degeneracy of the genetic code, and encode a glucose transporter encoded by isolated nucleic acids of (a) and (b) above. The isolated nucleic acid preferably encodes a mammalian GLUT 10 glucose transporter, and most preferably encodes a human GLUT 10 glucose transporter. The GLUT 10 glucose transporter is insulin responsive.

A further aspect of the present invention is a host cell transformed to contain an isolated nucleic acid encoding a GLUT 10 glucose transporter as described above.

A further aspect of the invention is a recombinant nucleic acid molecule comprising a promoter operatively associated with an isolated nucleic acid encoding a GLUT 10 glucose transporter as described above, along with host cells containing such recombinant nucleic acid, particularly host cells containing and expressing such the encoded glucose transporter.

A still further aspect of the invention is an isolated GLUT 10 glucose transporter protein encoded by a nucleic acid as described above.

A further aspect of the invention is an antibody that specifically binds to a GLUT 10 glucose transporter protein.

A further aspect of the invention is a method of screening substances as modulators of mammalian glucose transporter activity, comprising the steps of: providing a candidate compound; then contacting the candidate compound to (a) a glucose transporter protein encoded by a nucleic acid according to claim 1, or (b) a cell that contains and expresses the glucose transporter protein; and then determining the presence or absence of biochemical activity of the candidate compound on the glucose transporter, the presence of biochemical activity indicating the candidate compound is a modulator of glucose transporter activity. The biochemical activity may be binding, transporter translocation, responsiveness of the transporter to insulin, and transporter activity; the biochemical activity may be an inhibition or activation of the glucose transporter protien. The contacting step may be carried out under any suitable conditions, such as in a cell-free preparation comprising the glucose transporter (e.g., a cell membrane preparation), or in vitro in a preparation of cells that contain and express the nucleic acid.

A further aspect of the invention is a method of screening subjects for a glucose transporter disorder, comprising the steps of: determining the presence or absence of a decreased GLUT10 activity in the subject, the presence of decreased GLUT 10 activity indicating the subject is afflicted with or at risk of developing a glucose transporter disorder. The decreased activity may be decreased activity as compared to a subject that carries a GLUT 10 genes elected from the group consisting of (a) the GLUT 10 gene having the sequence given herein as SEQ ID NO: 1, and (b) GLUT 10 genes that hybridize to the complement of the sequence given herein as SEQ ID NO: 1 under stringent conditions and encode an insulin-responsive glucose transporter (and preferably as compared to (a)). The determining step may comprise the step of detecting a mutation in the GLUT 10 gene that decreases the expression or activity of the encoded glucose transporter, such as by detecting the presence or absence of a single nucleotide polymorphism in the GLUT10 gene of the subject, the single nucleotide polymorphism being a guanine to adenosine transition at base pair 616 of the GLUT 10 coding sequence, or a guanine to adenosine transition at base pair 859 of the GLUT 10 coding sequence, the presence of the single nucleotide polymorphism indicating the subject is afflicted with or at risk of developing a glucose transporter disorder (diabetes, type 2 diabetes). The determining step may be carried out by any suitable assay format, such as by collecting a biological sample from the subject, and then determining the presence or absence of a decreased GLUT10 activity from the biological sample. A further aspect of the present invention is a method of screening compounds for the ability to be transported across the cell membrane of cells that naturally express a GLUT 10 glucose transporter, the method comprising the steps of: providing a candidate compound; then contacting a glucose transporter protein encoded by a nucleic acid according to claim 1 with the candidate compound under conditions in which the transport of the candidate compound by the glucose transporter protein can be determined; and then determining the presence or absence of transport of the candidate compound by the glucose transporter protein, the presence of transport indicating that the compound will be transported across the cell membrane of cells that naturally express a GLUT 10 glucose transporter. The contacting step may be carried out in any suitable manner, such as in vitro in a preparation of cells that contain and express the nucleic acid, or carried out in vitro in a cell-free preparation comprising the glucose transporter (e.g., a proteoliposome preparation).

The foregoing and other objects and aspects of the present invention are explained in detail in the specification set forth below.

BRIEF DESCRIPTION OF THE DRAWINGS

FIG. 1B shows the nucleotide sequences of the exon/intron junctions are indicated. Exon sequences are shown in uppercase letters, intron sequences are shown in lowercase. For exon 5, the polyadenylation consensus sequence is underlined and the poly(A) tract is indicated.

FIG. 2A shows protein multiple sequence alignment of the GLUTn (n=1, 2, 3, 4, 5, 8, SEQ ID NOS: 38–43 respectively) family with the novel GLUT10 transporter (SEQ ID NO: 2). The alignment was generated using the pileup program (Genetics Computer Group, alignment penalties gap=10, extension=2) and ClustalX. Residues with blue background are identical to the consensus; green background are conserved residues with above average non-identity matrix scores; yellow residues are conserved with below average scores; white are neutral or non-conserved. Putative transmembrane domains were predicted using HMMTOP and TMHMM programs and are overlined. The long exofacial Loop9 between TMD9 and TMD10 separates two conserved blocks near GLUT10 residues 350 and 390.

FIG. 3 shows expression of GLUT10 mRNA in human tissues. (A) A full-length human GLUT10 cDNA was labeled and used to probe a commercially available Northern blot (Clontech 7760–1) containing 2 $\mu$g of poly(A) RNA from the indicated tissues. (B) RT-PCR analysis of GLUT10 expression in 24 human tissues. A human Rapid-Scan gene expression panel (OriGene Technologies) was used for PCR amplification with GLUT10-specific oligonucleotide primers. The tissue sources of the human cDNA are indicated. Parallel control reactions were performed with using water or human genomic DNA (Gen DNA). The PCR products were separated on a 1% agarose gel and visualized with ethidium bromide.

DETAILED DESCRIPTION OF PREFERRED EMBODIMENTS

Figure 1A:
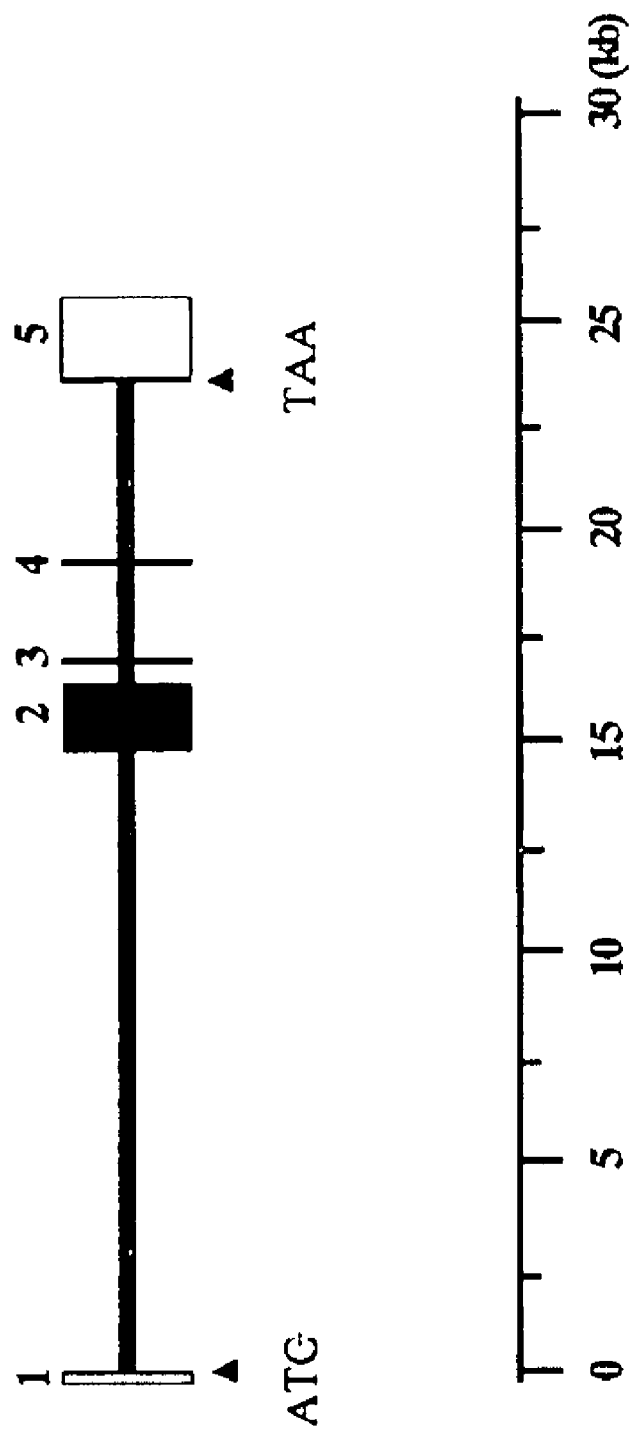
FIG. 1A depicts the structure of the human SLC2A10 gene (GLUT10). Exons are represented by the boxes and introns by the lines. The coding sequence in each exon is indicated by the shaded box, and the 3' untranslated region is denoted by the open box.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

The present investigations demonstrate that there is a novel human facilitative glucose transporter, designated GLUT10, in the Type 2 diabetes-linked region of human chromosome 20q12-13.1 between D20S888 and D20S891. The GLUT10 gene is encoded by 5 exons spanning 26.8 kb of genomic DNA. The GLUT10 cDNA encodes a 541 amino acid protein that shares between 30 and 33% amino acid identity with human GLUT1–8. The amino acid sequence predicts 12 transmembrane domains and shares characteristics of mammalian glucose transporters, including the GRR/K (between TM2 and TM3) and $EX_6R/K$ (between TM4 and TM5) motifs, conserved tryptophan residues (residues 430/454) critical for glucose transport activity, and two predicted N-linked glycosylation sites. Northern hybridization analysis identified a single 4.4 kb transcript for GLUT10 in heart, lung, brain, liver, skeletal muscle, pancreas, placenta, and kidney. By RT-PCR analysis, GLUT10 mRNA was also detected in fetal brain and liver. When expressed in *Xenopus* oocytes, GLUT10 exhibited 2-deoxy-D-glucose transport with an apparent $K_m$ of ~0.3 mM. D-glucose and D-galactose competed with 2-deoxy-D-glucose and transport was inhibited by phloretin. Pre-incubation with insulin stimulated glucose transport approximately 2-fold in oocytes injected with GLUT10 mRNA. Two SNPs are associated with Type 2 Diabetics in both Caucasian and African American populations.

The nucleic acid molecules of the invention and the polypeptides they encode (e.g., a GLUT10 polypeptide or fragments thereof) can be used directly as diagnostic and therapeutic agents, or they can be used to generate antibodies or identify small molecules that, in turn, are clinically useful. In addition, GLUT10 nucleic acid molecules can be used to identify the chromosomal location of GLUT10 and as tissue-specific markers. Accordingly, expression vectors containing the nucleic acid molecules of the invention, cells transfected with these vectors, the polypeptides expressed by these cells, and antibodies generated, against either the entire polypeptide or an antigenic fragment thereof, are among the preferred embodiments. These embodiments and some of their clinical application are described further below.

In Overview:

(1) The GLUT10 proteins and DNA sequences may be used to generate reagents for histological studies: (a) The protein sequence can be used to synthesize peptides to generate monospecific polyclonal or monoclonal antibodies. Such antibodies are useful as immunohistochemical or immunoblotting reagents in the diagnosis of insulin resistance and type 2 diabetes. (b) The DNA sequences can be used to synthesize oligonucleotide probes. Such probes are useful as research reagents for in situ hybridization, RNA blotting, and DNA blotting in the study of insulin resistance and type 2 diabetes. (c) The protein sequence can be used to synthesize peptides to generate monospecific polyclonal or monoclonal antibodies. Such antibodies are useful as immunohistochemical or immunoblotting reagents in the diagnosis of insulin resistance and type 2 diabetes.

(2) The GLUT10 nucleic acid sequences may be used to identify genetic markers for disorders such as diabetes linked to the GLUT10 gene.

(3) The GLUT10 protein sequence may be used to model the protein structure for use in activator design. Since GLUT10 is a very hydrophobic membrane glycoprotein, it is predicted to be extremely difficult to crystallize. It is unlikely that the 3-dimensional crystal structure of the protein will be solved anytime in the near future. The sequence of GLUT10 disclosed herein useful for designing new and potentially superior activators.

(4) The GLUT10 cDNA is useful for expression of large quantities of the GLUT10 protein in bacteria.

(5) The GLUT10 cDNA is useful for expression of large quantities of GLUT10 protein in recombinant baculovirus-infected insect cells.

(6) The GLUT10 cDNA is useful for stable expression of large quantities of the GLUT10 protein in mammalian tissue culture cells such as Chinese hamster ovary (CHO) cells, 3T3L1 fibroblasts, adipocytes, and L6 myoblasts.

(7) The GLUT10 cDNA is useful for stable expression of the GLUT10 protein in transgenic animals such as mice.

(8) Stably transfected GLUT10 over-expressing cell lines are useful for high throughput assays to screen combinatorial chemical libraries, fungal extracts, plant extracts, bacterial extracts, or higher eukaryotic cell extracts for potential activators or inhibitors of the GLUT10 glucose transporter for use as plasma glucose modulators.

(9) The wild type and polymorphic forms of GLUT10 cDNA are useful to generate fusion proteins such as GFP (Green Fluorescent Protein) fusions. These fusion proteins can be used to monitor the cellular distribution of GLUT10 and GLUT10 isoforms in response to exogenous hormones such as insulin, combinatorial chemical libraries, fungal extracts, plant extracts, bacterial extracts, or higher eukaryotic cell extracts. The goal of this high throughput screen would be to identify activators or inhibitors of the GLUT10 glucose transporter for use as plasma glucose modulators.

(10) The GLUT10 gene promoter may be fused to a reporter gene and stably transfected into mammalian tissue culture cells to screen combinatorial chemical libraries, fungal extracts, plant extracts, bacterial extracts, or higher eukaryotic cell extracts for agents that activate or inhibit GLUT10 gene expression to modulate plasma glucose levels.

(11) The GLUT10 cDNA may be used for gene therapy to restore glucose transporter activity to patients with type 1 or type 2 diabetes and impaired glucose utilization.

(12) GLUT10 may be used as a diagnostic marker for thyroid tumors. Some thyroid tumors are known to take up large amounts of fluorodeoxyglucose as detected by positron emission tomography scan. However, the identity of the glucose transporter responsible for this uptake was not clear since the known GLUTs (1–5) were not expressed in thyroid. However, we show that GLUT10 is expressed in thyroid and is most likely responsible for the fluorodeoxyglucose uptake by those thyroid tumors.

(13) GLUT10 nucleic acid may be used to develop gene-specific primers to detect GLUT10 polymorphisms that confer susceptibility to Type 2 diabetes.

Except as otherwise indicated, standard methods may be used for the production of cloned genes, expression cassettes, vectors, proteins and protein fragments, and transformed cells according to the present invention. Such techniques are known to those skilled in the art (see e.g., SAMBROOK et al., EDS., MOLECULAR CLONING: A LABORATORY MANUAL 2d ed. (Cold Spring Harbor, N.Y. 1989); F. M. AUSUBEL et al, EDS., CURRENT PROTOCOLS IN MOLECULAR BIOLOGY (Green Publishing Associates, Inc. and John Wiley & Sons, Inc., New York).

A. Definition of Terms

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., Patent In User Manual, pages D-2 to D3 (June 2000) (U.S. Patent and Trademark Office).

GLUT10, as used herein, refers to the amino acid sequence of substantially purified GLUT10 obtained from any species, particularly mammalian and preferably human, from any source whether natural, synthetic, semi-synthetic, or recombinant.

An "allele" or "allelic sequence," as used herein, is an alternative form of the gene encoding GLUT10. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Amino acid sequence", as used herein, refers to an oligopeptide, peptide, polypeptide, or protein sequence, and fragment thereof, and to naturally occurring or synthetic molecules. Fragments of GLUT10 are preferably about 5 to about 15 amino acids in length and retain the biological activity or the immunological activity of GLUT10. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

As used herein, the term "antibody" refers to intact molecules as well as fragments thereof, such as Fa, F(ab')$_2$, and Fc, which are capable of binding the epitopic determinant. Antibodies that bind GLUT10 polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands.

A "deletion", as used herein, refers to a change in the amino acid or nucleotide sequence and results in the absence of one or more amino acid residues or nucleotides.

The term "derivative", as used herein refers to the chemical modification of a nucleic acid encoding or complementary to GLUT10 or the encoded GLUT10. Such modifications include, for example, replacement of hydrogen by an alkyl, acyl, or amino group. A nucleic acid derivative encodes a polypeptide that retains the biological or immunological function of the natural molecule. A derivative polypeptide is one that is modified by glycosylation, pegylation, or any similar process that retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences that are greater than 20, 40 or 60 nucleotides than in length, up to 200 or 400 nucleotides in length or more.

The term "oligonucleotide" refers to a nucleic acid sequence of at least about 6 or 12 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

The term "biological sample", as used herein, is used in its broadest sense. A biological sample suspected of containing nucleic acid encoding GLUT10, or fragments thereof, or GLUT10 itself may comprise a bodily fluid, extract from a cell, chromosome, organelle, or membrane isolated from a cell, a cell, genomic DNA, RNA, or cDNA (in solution or bound to a solid support, a tissue, a tissue print, and the like). The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors may be varied to generate conditions of either low or high stringency different from, but equivalent to, the above listed conditions.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, direct DNA injection (e.g., into muscle tissue) and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

B. Nucleic Acids Encoding GLUT10

Polynucleotides of the present invention include those coding for proteins homologous to, and having essentially the same biological properties as, the proteins disclosed herein, and particularly the DNA disclosed herein as SEQ ID NO:1 and encoding the protein GLUT10 given herein SEQ ID NO:2. This definition is intended to encompass natural allelic sequences thereof. Thus, isolated DNA or cloned genes of the present invention can be of any species of origin, preferably of mammalian origin. Thus, polynucleotides that hybridize to DNA disclosed herein as SEQ ID NO:1 (or fragments or derivatives thereof which serve as hybridization probes as discussed below) and which code on expression for a protein of the present invention (e.g., a protein according to SEQ ID NO:2) are also an aspect of the invention. Conditions which will permit other polynucleotides that code on expression for a protein of the present invention to hybridize to the DNA of SEQ ID NO:1 disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1×SSPE at 37° C.; conditions represented by a wash stringency of 40–45% Formamide with 5× Denhardt's solution, 0.5% SDS, and 1×SSPE at 42° C.; and conditions represented by a wash stringency of 50% Formamide with 5× Denhardt's solution, 0.5% SDS and 1×SSPE at 42° C., respectively) to DNA of SEQ ID NO:1 disclosed herein in a standard hybridization assay. See, e.g., J. Sambrook et al., *Molecular Cloning, A Laboratory Manual* (2d Ed. 1989) (Cold Spring Harbor Laboratory). In general, sequences which code for proteins of the present invention and which hybridize to the DNA of SEQ ID NO:1 disclosed herein will be at least 75% homologous, 85% homologous, and even 95% homologous or more with SEQ ID NO:1. Further, polynucleotides that code for proteins of the present invention, or polynucleotides that hybridize to that as SEQ ID NO:1, but which differ in codon sequence from SEQ ID NO:1 due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

Although nucleotide sequences which encode GLUT10 and its variants are preferably capable of hybridizing to the nucleotide sequence of the naturally occurring GLUT10 under appropriately selected conditions of stringency, it may be advantageous to produce nucleotide sequences encoding GLUT10 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GLUT10 and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode GLUT10 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding GLUT10 or any fragment thereof.

Knowledge of the nucleotide sequence as disclosed herein in SEQ ID NO:1 can be used to generate hybridization probes which specifically bind to the DNA of the present invention or to mRNA to determine the presence of amplification or overexpression of the proteins of the present invention.

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

Methods for DNA sequencing which are well known and generally available in the art may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding GLUT10 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

C. Vectors and Host Cells Containing Nucleic Acid Sequences Encoding GLUT10

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites that are operably linked to the gene to be expressed and are operable in the host organism.

DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells are cells which have been transformed or transfected with vectors containing DNA coding for proteins of the present invention need not express protein.

Suitable host cells include prokaryotes, yeast cells, or higher eukaryotic organism cells. Prokaryote host cells include gram negative or gram positive organisms, for example *Escherichia coli* (*E. coli*) or *Bacilli*. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. See Bolivar et al., *Gene* 2, 95 (1977). Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983). The promoter and Shine-Dalgarno sequence (for prokaryotic host expression) are operably linked to the DNA of the present invention, i.e., they are positioned so as to promote transcription of the messenger RNA from the DNA.

Expression vectors should contain a promoter that is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980). The promoter and Shine-Dalgarno sequence (for prokaryotic host expression) are operably linked to the DNA encoding the desired protein, i.e., they are positioned so as to promote transcription of the protein messenger RNA from the DNA.

Eukaryotic microbes such as yeast cultures may be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977). The presence of the trp1 lesion in the yeast host cell genome then provides an effective environment for detecting transformation by growth in the absence of tryptophan.

Suitable promoting sequences in yeast vectors include the promoters for metallothionein, 3-phospho-glycerate kinase (Hitzeman et al., *J. Biol. Chem.* 255, 2073 (1980) or other glycolytic enzymes (Hess et al., *J Adv. Enzyme Reg.* 7, 149 (1968); and Holland et al., *Biochemistry* 17, 4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant protein synthesis. In principal, any higher eukaryotic cell culture is workable, whether from vertebrate or invertebrate culture, including insect cells.

Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and W1138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment that also contains the SV40 viral origin of replication. See Fiers et al., *Nature* 273, 113 (1978). Further, the protein promoter, control and/or signal sequences may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculorivus expression vector (e.g., vectors derived from *Autographa californica* MNPV, *Trichoplusia ni* MNPV, *Rachiplusia ou* MNPV, or *Galleria ou* PV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

In mammalian host cells, a number of viral-based expression systems may be utilized. In cases where an adenovirus is used as an expression vector, sequences encoding GLUT10 may be ligated into an adenovirus transcription/translation complex consisting of the late promoter and tripartite leader sequence. Insertion in a non-essential E1 or E3 region of the viral genome may be used to obtain a viable virus which is capable of expressing GLUT10 in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Rather than using vectors that contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to lake up exogenous DNA. Generally, identification is by survival or transformants in culture medium that is toxic, or from which the cells cannot obtain critical nutrition without having taken up the marker protein.

D. GLUT10 Protein Expression

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/ hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; KGln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

As noted above, the present invention provides isolated and purified GLUT10 proteins, such as mammalian (or more preferably human) GLUT10. Such proteins can be purified from host cells which express the same, in accordance with known techniques, or even manufactured synthetically.

Nucleic acids of the present invention, constructs containing the same, and host cells that express the encoded proteins are useful for making proteins of the present invention.

Specific initiation signals may also be used to achieve more efficient translation of sequences encoding GLUT10. Such signals include the ATG initiation codon and adjacent sequences. In cases where sequences encoding GLUT10, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express GLUT10 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk- or aprt-cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed.

For example, if the sequence encoding GLUT10 is inserted within a marker gene sequence, transformed cells containing sequences encoding GLUT10 can be identified by the absence of marker gene function. Alternatively, a marker gene can be placed in tandem with a sequence encoding GLUT10 under the control of a single promoter. Expression of the marker gene in response to induction or selection usually indicates expression of the tandem gene as well.

Alternatively, host cells which contain the nucleic acid sequence encoding GLUT 10 and express GLUT 10 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding GLUT10 can be detected by DNA-DNA or DNA-RNA hybridization or amplification using probes or fragments or fragments of polynucleotides encoding GLUT10. Nucleic acid amplification based assays involve the use of oligonucleotides or oligomers based on the sequences encoding GLUT10 to detect transformants containing DNA or RNA encoding GLUT10.

A variety of protocols for detecting and measuring the expression of GLUT10, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on GLUT10 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; *J. Exp. Med* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding GLUT10 include oligolabeling, nick translation, end-labeling or PCR amplification using a labeled nucleotide. Alternatively, the sequences encoding GLUT10, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding GLUT10 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode GLUT10 may be designed to contain signal sequences which direct secretion of GLUT10 through a prokaryotic or eukaryotic cell membrane. Other constructions may be used to join sequences encoding GLUT10 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and GLUT10 may be used to facilitate purification. One such expression vector provides for expression of a fusion protein containing GLUT10 and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263–281) while the enterokinase cleavage site provides a means for purifying GLUT10 from the fusion protein. A discussion of vectors which contain fusion proteins is provided in Kroll, D. J. et al. (1993; DNA Cell Biol. 12:441–453).

In addition to recombinant production, fragments of GLUT10 may be produced by direct peptide synthesis using solid-phase techniques (Merrifield J. (1963) *J. Am. Chem. Soc.* 85, 2149–2154). Protein synthesis may be performed using manual techniques or by automation. Automated synthesis may be achieved, for example, using Applied Biosystems 431A Peptide Synthesizer (Perkin Elmer). Various fragments of GLUT10 may be chemically-synthesized separately and combined using chemical methods to produce the full-length molecule.

E. Transgenic Animals

GLUT10 polypeptides can also be expressed in transgenic animals. Such transgenic animals represent model systems for the study of disorders that are either caused by or exacerbated by misexpression of GLUT10, or disorders that can be treated by altering the expression of GLUT10 or the activity of GLUT10 (even though the expression or activity is not detectably abnormal). Transgenic animals can also be used for the development of therapeutic agents that modulate the expression of GLUT10 or the activity of GLUT10.

Transgenic animals can be farm animals (e.g., pigs, goats, sheep, cows, horses, rabbits, and the like) rodents (such as rats, guinea pigs, and mice), non-human primates (e.g., baboons, monkeys, and chimpanzees), and domestic animals (e.g., dogs and cats). Transgenic mice are especially preferred.

Any technique known in the art can be used to introduce a GLUT10 transgene into animals to produce founder lines of transgenic animals. Such techniques include, but are not limited to, pronuclear microinjection (U.S. Pat. No. 4,873, 191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983).

The present invention provides for transgenic animals that carry a GLUT10 transgene in all of their cells, as well as animals that carry a transgene in some, but not all of their cells. For example, the invention provides for mosaic animals. The GLUT10 transgene can be integrated as a single transgene or in concatamers, for example, head-to-head tandems or head-to-tail tandems. The transgene can also be selectively introduced into, and activated in, a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that a GLUT10 transgene be integrated into the chromosomal site of an endogenous GLUT10 gene, gene targeting is preferred. Briefly, when such a technique is to be used, vectors containing some nucleotide sequences homologous to an endogenous GLUT10 gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous GLUT10 gene in only that cell type (Gu et al., *Science* 265:103, 1984). The regulatory sequences required for such a cell-type specific inactivation will depend upon the particular cell type of interest, and will be apparent to those of skill in the art. These techniques are useful for preparing "knock outs" having no functional GLUT10 gene.

Once transgenic animals have been generated, the expression of the recombinant GLUT10 gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, northern blot analysis of tissue samples obtained from the animal, in situ hybridization analysis, and RT-PCR. Samples of GLUT10 gene-expressing tissue can also be evaluated immunocytochemically using antibodies specific for the GLUT10 transgene product.

For a review of techniques that can be used to generate and assess transgenic animals, consult Gordon (*Intl. Rev. Cytol.* 115:171–229, 1989), and may obtain additional guidance from, for example: Hogan et al. "Manipulating the Mouse Embryo" (Cold Spring Harbor Press, Cold Spring Harbor, N.Y., 1986); Krimpenfort et al., *Bio/Technology* 9:86, 1991; Palmiter et al., *Cell* 41:343, 1985; Kraemer et al., "Genetic Manipulation of the Early Mammalian Embryo," Cold Spring Harbor Press, Cold Spring Harbor, N.Y., 1985; Hammer et al., *Nature* 315:680, 1985; Purcel et al., *Science* 244:1281, 1986; Wagner et al., U.S. Pat. No. 5,175,385; and Krimpenfort et al., U.S. Pat. No. 5,175,384.

The transgenic animals of the invention can be used to determine the consequence of altering the expression of GLUT10 in the context of various disease states. For example, GLUT10 knock out mice can be generated using an established line of mice that serve as a model for a disease in which activity of the missing gene is impaired.

F. Antibodies to GLUT10 Protein

Antibodies that specifically bind to the proteins of the present invention (i.e., antibodies which bind to a single antigenic site or epitope on the proteins) are useful for a variety of purposes.

Antibodies to GLUT10 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with GLUT10 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface-active substances such as lysolecithin, pluronic polyols, polyanions, peptides, oil emulsions, keyhole limpet hemocyanin, and dinitrophenol. Among adjuvants used in humans, BCG (*bacilli* Calmette-Guerin) and *Corynebacterium parvum* are especially preferable.

It is preferred that the oligopeptides, peptides, or fragments used to induce antibodies to GLUT10 have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of GLUT10 amino acids may be fused with those of another protein such as keyhole limpet hemocyanin and antibody produced against the chimeric molecule.

Monoclonal antibodies to GLUT10 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495497; Kozbor, D. et al. (1985) J. Immunol. Methods 81:3142; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) *Proc. Natl. Acad. Sci.* 81, 6851–6855; Neuberger, M. S. et al. (1984) *Nature* 312:604–608; Takeda, S. et al. (1985) *Nature* 314:452–454). Alternatively, techniques described for the production of single chain antibodies may be adapted, using methods known in the art, to produce GLUT 10-specific single chain antibodies. Antibodies with related specificity, but of distinct idiotypic composition, may be generated by chain shuffling from random combinatorial immunoglobin libraries (Burton D. R. (1991) *Proc. Natl. Acad. Sci.* 88,11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) *Nature* 349:293–299).

Antibody fragments, which contain specific binding sites for GLUT10, may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificity are well known in the art. Such immunoassays typically involve the measurement of complex formation between GLUT10 and its specific antibody. A two-site, monoclonal-based immunoassay utilizing monoclonal antibodies reactive to two non-interfering GLUT10 epitopes is preferred, but a competitive binding assay may also be employed (Maddox, supra).

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

G. Assays Detecting Nucleic Acids Encoding GLUT10 and GLUT10 Protein

Kits for determining if a sample contains proteins of the present invention will include at least one reagent specific for detecting the presence or absence of the protein. Diagnostic kits for carrying out antibody assays may be produced in a number of ways. In one embodiment, the diagnostic kit comprises (a) an antibody which binds proteins of the present invention conjugated to a solid support and (b) a second antibody which binds proteins of the present invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. A second embodiment of a test kit comprises (a) an antibody as above, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

Assays for detecting the polynucleotide encoding GLUT10 in a cell, or the extent of amplification thereof, typically involve, first, contacting the cells or extracts of the cells containing nucleic acids therefrom with an oligonucleotide that specifically binds to GLUT10 polynucleotide as given herein (typically under conditions that permit access of the oligonucleotide to intracellular material), and then detecting the presence or absence of binding of the oligonucleotide thereto. Again, any suitable assay format may be employed (see, e.g., U.S. Pat. No. 4,358,535 to Falkow et al.; U.S. Pat. No. 4,302,204 to Wahl et al.; U.S. Pat. No. 4,994,373 to Stavrianopoulos et al; U.S. Pat. No. 4,486,539 to Ranki et al.; U.S. Pat. No. 4,563,419 to Ranki et al.; and U.S. Pat. No. 4,868,104 to Kurn et al.) (the disclosures of which applicant specifically intends be incorporated herein by reference).

H. Antisense Oligonucleotides

Antisense oligonucleotides and nucleic acids that express the same may be made in accordance with conventional techniques. See, e.g., U.S. Pat. No. 5,023,243 to Tullis; U.S. Pat. No. 5,149,797 to Pederson et al. The length of the antisense oligonucleotide (i.e., the number of nucleotides therein) is not critical so long as it binds selectively to the intended location, and can be determined in accordance with routine procedures. In general, the antisense oligonucleotide will be from 8, 10 or 12 nucleotides in length up to 20, 30, or 50 nucleotides in length.

Treatment regimes based on an "antisense" approach involve the design of oligonucleotides (either DNA or RNA) that are complementary to a portion of a selected mRNA. These oligonucleotides bind to complementary mRNA transcripts and prevent their translation. Absolute complementarity, although preferred, is not required. A sequence "complementary" to a portion of an RNA molecule, as referred to herein, is a sequence having sufficient complementarily to hybridize with the RNA, forming a stable duplex; in the case of double-stranded antisense nucleic acids, a single strand of the duplex DNA can be tested, or triplex formation can be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One of ordinary skill in the art can ascertain a tolerable degree of mismatch by use of standard procedures to determine the melting point of the hybridized complex.

It is preferred that therapeutic strategies directed to GLUT10, be performed first in vitro to assess the ability of an antisense oligonucleotide to inhibit gene expression. If desired, the assessment can be quantitative. It is preferred that these studies utilize controls that distinguish between antisense gene inhibition and any nonspecific biological effect that an oligonucleotide may cause. It is also preferred that these studies compare levels of the target RNA or protein with that of an internal control RNA or protein. Additionally, it is envisioned that results obtained using an antisense oligonucleotide are compared with those obtained using a control oligonucleotide. Preferably, the control oligonucleotide is of approximately the same length as the test oligonucleotide, and the nucleotide sequence of the control oligonucleotide differs from that of the test antisense sequence no more than is necessary to prevent specific hybridization between the control oligonucleotide and the targeted RNA sequence.

The oligonucleotides can contain DNA or RNA, or they can contain chimeric mixtures, derivatives, or modified versions thereof that are either single-stranded or double-stranded. The oligonucleotide can be modified at the base moiety, sugar moiety, or phosphate backbone, for example, to improve stability of the molecule, hybridization, etc. Modified sugar moieties can be selected from the group including, but not limited to, arabinose, 2-fluoroarabinose, xylulose, and hexose. A modified phosphate backbone can be selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones. In another non-limiting example, such antisense oligonucleotides are oligonucleotides wherein at least one, or all, of the nucleotides contain a 2' lower alkyl moiety (e.g., $C_1$–$C_4$, linear or branched, saturated or unsaturated alkyl, such as methyl, ethyl, ethenyl, propyl, 1-propenyl, 2-propenyl, and isopropyl). For example, every other one of the nucleotides may be modified as described. See also P. Furdon et al., *Nucleic Acids Res.* 17, 9193–9204 (1989); S. Agrawal et al., *Proc. Natl. Acad. Sci. USA* 87, 1401–1405 (1990); C. Baker et al., *Nucleic Acids Res.* 18, 3537–3543 (1990); B. Sproat et al., *Nucleic Acids Res.* 17, 3373–3386 (1989); R. Walder and J. Walder, *Proc. Natl. Acad. Sci. USA* 85, 5011–5015 (1988).

The oligonucleotide can include other appended groups such as peptides (e.g., for disrupting the transport properties of the molecule in host cells in vivo), or agents that facilitate transport across the cell membrane (as described, for example, in Letsinger et al., *Proc. Natl. Acad. Sci. USA* 86:6553, 1989; Lemaitre et al., *Proc. Natl. Acad. Sci. USA* 84:648, 1987; PCT Publication No. WO 88/09810) or the blood-brain barrier (see, for example, PCT Publication No. WO 89/10134), or hybridization-triggered cleavage agents (see, for example, Krol et al., *BioTechniques* 6:958, 1988), or intercalating agents (see, for example, Zon, Pharm. Res. 5:539, 1988). To this end, the oligonucleotide can be conjugated to another molecule, for example, a peptide, a hybridization triggered cross-linking agent, a transport agent, or a hybridization-triggered cleavage agent.

For therapeutic application, antisense molecules of the invention should be delivered to cells that express GLUT10 in vivo. A number of methods have been developed for delivering antisense DNA or RNA to cells; for example, antisense molecules can be injected directly into the tissue site. Alternatively, modified antisense molecules, which are designed to target cells that express GLUT10 (e.g., antisense molecules linked to peptides or antibodies that specifically bind receptors or antigens expressed on the target cell surface) can be administered systemically.

However, it is often difficult to achieve intracellular concentrations of antisense molecules that are sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with endogenous GLUT10 transcripts and thereby prevent translation of GLUT10 mRNA. For example, a vector can be introduced in vivo in such a way that it is taken up by a cell and thereafter directs the transcription of an antisense RNA. Such a vector can remain episomal or become chromosomally-integrated, as long as it can be transcribed to produce the desired antisense RNA.

Vectors encoding a GLUT10 antisense sequence can be constructed by recombinant DNA technology methods that are standard practice in the art. Suitable vectors include plasmid vectors, viral vectors, or other types of vectors known or newly discovered in the art. The criterion for use is only that the vector be capable of replicating and expressing the GLUT10 antisense molecule in mammalian cells. Expression of the sequence encoding the antisense RNA can be directed by any promoter known in the art to act in mammalian, and preferably in human, cells. Such promoters can be inducible or constitutively-active and include, but are not limited to: the SV40 early promoter region (Bernoist et al., Nature 290:304, 1981); the promoter contained in the 3' long terminal
repeat of Rous sarcoma virus (Yamamoto et al., Cell 22:787–797, 1988); the herpes thymidine kinase promoter (Wagner et al., Proc. Natl. Acad. Sci. USA 78:1441, 1981); or the regulatory sequences of the metallothionein gene (Brinster et al., Nature 296:39, 1988).

I. Ribozymes

Ribozyme molecules designed to catalytically-cleave GLUT10 mRNA transcripts also can be used to prevent translation of GLUT10 mRNA and expression of GLUT10 polypeptides (see, for example, PCT Publication WO 90/11364; Saraver et al., Science 247:1222, 1990). While various ribozymes that cleave mRNA at site-specific recognition sequences can be used to destroy GLUT10 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., Nature 334:585, 1988). There are numerous examples of potential hammerhead ribozyme cleavage sites within the nucleotide sequence of human GLUT10 cDNA. Preferably, the ribozyme is engineered so that the cleavage recognition site is located near the 5' end of the GLUT10 mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in Tetrahymena Thermophila (known as the IVS or L-19 IVS RNA), and which has been extensively described by Cech and his collaborators (Zaug et al., Science 224:574, 1984; Zaug et al., Science 231:470, 1986; Zug et al., Nature 324:429, 1986; PCT Application No. WO 88/04300; and Been et al., Cell 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in GLUT10.

As in the antisense approach, the ribozymes can be composed of modified oligonucleotides (e.g., for improved stability, targeting, etc.), and should be delivered to cells which express the GLUT10 in vivo. A preferred method of delivery involves using a DNA construct "encoding" the ribozyme under the control of a strong constitutive pol III or pol II promoter, so that transfected cells will produce sufficient quantities of the ribozyme to destroy endogenous GLUT10 messages and inhibit translation. Because ribozymes, unlike antisense molecules, are catalytic, a lower intracellular concentration is required for efficiency.

J. Peptide Nucleic Acids

Nucleic acid molecules encoding GLUT10 (or a fragment thereof) can be modified at the base moiety, sugar moiety, or phosphate backbone to improve, for example, the stability or solubility of the molecule or its ability to hybridize with other nucleic acid molecules. For example, the deoxyribose phosphate backbone of the nucleic acid can be modified to generate peptide nucleic acids (see Hyrup et al., Bioorganic Med. Chem. 4:5–23 (1996). As used herein, the terms "peptide nucleic acids" or "PNAs" refer to nucleic acid mimics, for example, DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., supra; Perry-O'Keefe et al. Proc. Natl. Acad. Sci. USA 93:14670–14675 (1996).

PNAs of GLUT10 can be used in therapeutic and diagnostic applications. For example, PNAs can be used as antisense or antigene agents for sequence-specific modulation of gene expression by, for example, inducing transcription or translation arrest or inhibiting replication. PNAs of GLUT10 can also be used, for example, in the analysis of single base pair mutations in a gene by, for example, PNA-directed PCR clamping; as artificial restriction enzymes when used in combination with other enzymes, for example, S1 nucleases (Hyrup et al., supra); or as probes or primers for DNA sequence and hybridization (Hyrup et al., supra; Perry-O'Keefe, supra).

In other embodiments, PNAs of GLUT10 can be modified, for example, to enhance their stability or cellular uptake, by attaching lipophilic or other helper groups to the PNA, by the formation of PNA-DNA chimeras, or by the use of liposomes or other techniques of drug delivery known in the art. For example, PNA-DNA chimeras of GLUT10 can be generated that may combine the advantageous properties of PNA and DNA. Such chimeras allow DNA recognition enzymes, for example, RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup et al., supra). The synthesis of PNA-DNA chimeras can be performed as described in Hyrup, supra, and Finn et al., Nucl. Acids Res. 24:3357–3363 (1996). For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used between the PNA and the 5' end of DNA (Mag et al., Nucl. Acids Res. 17:5973–5988, 1989). PNA monomers are then coupled in a stepwise manner to produce a chimeric molecule with a 5' PNA segment and a 3' DNA segment (Finn et al., supra).

Alternatively, chimeric molecules can be synthesized with a 5' DNA segment and a 3' PNA segment (Peterser et al., *Bioorganic Med. Chem. Lett.* 5:1119–11124 (1975).

In other embodiments, the oligonucleotide may include other appended groups such as peptides (e.g., for targeting host cell receptors in vivo), or agents facilitating transport across the cell membrane (see, e.g., Letsinger et al., *Proc. Natl. Acad. Sci.* USA 86:6553–6556 (1989); Lemaitre et al., *Proc. Natl. Acad. Sci. USA* 84:648–652 (1987); PCT Publication No. WO 88/09810, published Dec. 15, 1988) or the blood-brain barrier (see, e.g., PCT Publication No. WO 89/10134, published Apr. 25, 1988). In addition, oligonucleotides can be modified with hybridization-triggered cleavage agents (see, e.g., Krol et al., *BioTech.* 6:958–976 (1988)) or integrating agents (see, e.g., Zon, *Pharm. Res.* 5:539–549 (1988)). To this end, the oligonucleotide may be conjugated to another molecule, for example, a peptide, hybridization triggered cross-linking agent, transport agent, hybridization-triggered cleavage agent etc.

K. Diagnostic and Prognostic Assays

The invention also encompasses screening assays, including diagnostic and prognostic assays that can be used to identify subjects having or at risk of developing a disease or disorder associated with aberrant GLUT10 expression or GLUT10 activity. Thus, the present invention provides methods in which a sample is obtained from a subject and the level, or presence, or allelic form GLUT10 nucleic acid molecules or GLUT10 polypeptides is assessed.

Furthermore, the assays described herein can be used to determine whether a subject can be administered an agent (e.g., an agonist, antagonist, peptidomimetic, polypeptide, nucleic acid, small molecule or other drug candidate) to treat a disease or disorder associated with aberrant GLUT10 expression or GLUT10 activity. For example, such methods can be used to determine whether a subject can be effectively treated with an agent that modulates GLUT10 expression and/or activity. Thus, the present invention provides methods for determining whether a subject can be effectively treated with an agent for a disorder associated with aberrant GLUT10 expression or GLUT10 activity in which a sample is obtained and GLUT10 nucleic acids or GLUT10 polypeptides are detected (e.g., wherein the presence of a particular level of GLUT10 expression or a particular GLUT10 allelic variant is diagnostic for a subject that can be administered an agent to treat a disorder associated with aberrant GLUT10 expression or GLUT10 activity).

The methods of the invention can also be used to detect genetic alterations in a GLUT10. In preferred embodiments, the methods include detecting, in a sample of cells from the subject, the presence or absence of a genetic alteration characterized by at least one alteration affecting the integrity of the gene encoding a GLUT10 polypeptide or the misexpression of the GLUT10 gene. For example, such genetic alterations can be detected by ascertaining the existence of at least one of: (1) a deletion of one or more nucleotides from a GLUT10 gene; (2) an addition of one or more nucleotides to a GLUT10 gene; (3) a substitution of one or more nucleotides of a GLUT10 gene; (4) a chromosomal rearrangement of a GLUT10 gene; (5) an alteration in the level of a messenger RNA transcript of a GLUT10 gene; (6) aberrant modification of a GLUT10 gene, such as of the methylation pattern of the genomic DNA, (7) the presence of a non-wild type splicing pattern of a messenger RNA transcript of a GLUT10 gene; and (10) inappropriate post-translational modification of a GLUT10 polypeptide. As described herein, there are a large number of assay techniques known in the art which can be used for detecting alterations in a GLUT10 gene.

In certain embodiments, detection of the alteration involves the use of a probe/primer in a polymerase chain reaction (PCR; see, e.g., U.S. Pat. Nos. 4,683,195 and 4,683,202), such as anchor PCR or RACE PCR, or alternatively, in a ligation chain reaction (LCR; see, e.g., Landegran et al., *Science* 241:1077–1080, 1988; and Nakazawa et al. *Proc. Natl. Acad. Sci USA* 91:360–364, 1994), the latter of which can be particularly useful for detecting point mutations in the GLUT10 gene (see Abavaya et al., *Nucl. Acids Res.* 23:675–681, 1995). This method can include the steps of collecting a sample of cells from a patient, isolating nucleic acid (e.g., genomic DNA, mRNA, or both) from the cells of the sample, contacting the nucleic acid sample with one or more primers which specifically hybridize to a GLUT10 gene under conditions such that hybridization and amplification of the GLUT10 nucleic acid (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli et al., *Proc. Natl. Acad. Sci USA* 87:1874–1878, 1990), transcriptional amplification system (Kwoh et al., Proc. Natl. Acad. Sci USA 86:1173–1177, 1989), Q-Beta Replicase (Lizardi et al., Bio/Technology 6:1197, 1988), or any other nucleic acid amplification method, followed by the detection of the amplified molecules using techniques well known to those of ordinary skill in the art. These detection schemes are especially useful for the detection of nucleic acid molecules if such molecules are present in very low number.

In an alternative embodiment, alterations in a GLUT10 gene from a sample cell can be identified by identifying changes in a restriction enzyme cleavage pattern. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498, 531) can be used to score for the presence of specific mutations by development or loss of a ribozyme cleavage site.

In other embodiments, alterations in GLUT10 can be identified by hybridizing a sample and control nucleic acids, e.g., DNA or RNA, to high density arrays containing tens to thousands of oligonucleotide probes (Cronin et al., *Human Mutation* 7:244–255, 1996); Kozal et al., *Nature Medicine* 2:753–759, 1996). For example, alterations in GLUT10 can be identified in two dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the GLUT10 gene and detect mutations by comparing the sequence of the sample GLUT10 with the corresponding wild-type (control) sequence. Examples of sequencing reactions include those based on techniques developed by Maxim and Gilbert (*Proc. Natl. Acad. Sci. USA* 74:560 (1977)) or Sanger (*Proc. Natl. Acad. Sci. USA* 74:5463). It is also contemplated that any of a variety of automated sequencing procedures can be utilized when performing the diagnostic assays (*Bio/Techniques* 19:448, 1995) including sequencing by mass spectrometry (see, e.g. PCT International Publication No. WO 94/16101; Cohen et al. *Adv. Chromatogr.* 36:127–162 1996; and Griffin et al., *Appl. Biochem. Biotechnol.* 38:147–159, 1993).

Other methods of detecting mutations in the GLUT 10 gene include methods in which protection from cleavage agents is used to detect mismatched bases in RNA/RNA or RNA/DNA heteroduplexes (Myers et al. *Science* 230:1242 1985). In general, the art technique of "mismatch cleavage" starts by providing heteroduplexes formed by hybridizing (labeled) RNA or DNA containing the wild-type GLUT10 sequence with potentially mutant RNA or DNA obtained from a tissue sample. The double-stranded duplexes are treated with an agent which cleaves single-stranded regions of the duplex such as which will exist due to base-pair mismatches between the control and sample strands. For instance, RNA/DNA duplexes can be treated with RNase and DNA/DNA hybrids treated with S1 nuclease to enzymatically-digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. (see, for example, Cotton et al., *Proc. Natl. Acad. Sci. USA* 85:4397 1988; Saleeba et al., *Methods Enzymol.* 217:286–295 1992). In a preferred embodiment, the control DNA or RNA can be labeled for detection.

In still another embodiment, the mismatch cleavage reaction employs one or more proteins that recognize mismatched base-pairs in double-stranded DNA (so called "DNA mismatch repair" enzymes) in defined systems for detecting and mapping point mutations in GLUT10 cDNAs obtained from samples of cells. For example, the mutY enzyme of *E. coli* cleaves A at G/A mismatches (Hsu et al., *Carcinogenesis* 15:1657–1662 1994). According to an exemplary embodiment, a probe based on a GLUT10 sequence is hybridized to a CDNA or other DNA product from a test cell or cells. The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility can be used to identify mutations in GLUT10 genes. For example, single strand conformation polymorphism (SSCP) can be used to detect differences in electrophoretic mobility between mutant and wild type nucleic acids (Orita et al., *Proc. Natl. Acad. Sci. USA* 86:2766, see also Cotton *Mutat Res.* 285:125–144 1993; and Hayashi *Genet. Anal. Tech. Appl.* 9:73–79 1992). Single-stranded DNA fragments of sample and control GLUT10 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the method utilizes heteroduplex analysis to separate double stranded heteroduplex molecules on the basis of changes in electrophoretic mobility (Kee et al., *Trends Genet.* 7:5 1991).

In yet another embodiment, the movement of mutant or wild-type fragments in a polyacrylamide gel containing a gradient of denaturant is assayed using denaturing gradient gel electrophoresis (DGGE; Myers et al., *Nature* 313:495, 1985). When DGGE is used as the method of analysis, DNA will be modified to insure that it does not completely denture, for example by adding a GC clamp of approximately 40-bp of high-melting GC-rich DNA by PCR. In a further embodiment, a temperature gradient is used in place of a denaturing gradient to identify differences in the mobility of control and sample DNA (Rosenbaum et al., *Biophys. Chem.* 265:12753, 1987).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al., *Nature* 324;163, 1986); Saiki et al., *Proc. Natl. Acad. Sci. USA* 86:6230, 1989). Such allele-specific oligonucleotides are hybridized to PCR amplified target DNA or a number of different mutations when the oligonucleotides are attached to the hybridizing membrane and hybridized with labeled target DNA.

Alternatively, allele-specific amplification technology which depends on selective PCR amplification may be used in conjunction with the instant invention. Oligonucleotides used as primers for specific amplification may carry the mutation of interest in the center of the molecule, so that amplification depends on differential hybridization (Gibbs et al., *Nucl. Acids Res.* 17:2437–2448, 1989) or at the extreme 3' end of one primer where, under appropriate conditions, mismatch can prevent, or reduce polymerase extension (Prossner, *Tib/Tech* 11:238, 1993). In addition it may be desirable to introduce a novel restriction site in the region of the mutation to create cleavage-based detection (Gasparini et al., *Mol. Cell Probes* 6:1, 1992). It is anticipated that in certain embodiments amplification may also be performed using Taq ligase for amplification (Barany, *Proc. Natl. Acad. Sci. USA* 88:89, 1991). In such cases, ligation will occur only if there is a perfect match at the 3' end of the 5' sequence making it possible to detect the presence of a known mutation at a specific site by looking for the presence of absence of amplification.

The methods described herein may be performed, for example, by utilizing pre-packaged diagnostic kits comprising at least one probe nucleic acid or antibody reagent described herein, which may be conveniently used, for example, in a clinical setting to diagnose patient exhibiting symptoms or a family history of a disease or disorder involving abnormal GLUT10 activity.

L. Gene Therapy.

The nucleic acids and nucleic acid constructs of the present invention can be administered to subjects in a suitable vector or pharmaceutically acceptable formulation to increase the expression of the encoded GLUT 10 glucose transporter in sufficient cells of the subject to treat (i.e., reduce the severity of symptoms) diabetes, including both type 1 and type 2 diabetes. Any suitable target tissue or cells in the subject may be transformed, with muscle cells and tissues being particularly preferred. Administration may be by any suitable technique, such as by the direct injection of DNA encoding the glucose transporter described herein into muscle of the subject so that the DNA is expressed in the muscle of the subject, such as described in U.S. Pat. No. 5,580,859 to Felgner et al., the disclosure of which is incorporated herein by reference. Any suitable dosage regimen may be employed, depending upon the condition of the subject and the severity of the conditions, such as multiple direct injections into large muscle groups such as the quadriceps.

M. Pharmacological Applications

In another embodiment of the invention, GLUT10, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between GLUT10 and the agent being tested, may be measured.

Another technique for drug screening that may be used provides for high throughput screening of compounds having suitable binding affinity to the protein of interest as described in published PCT application WO84/03564. In this method, as applied to GLUT10, large numbers of different small test compounds are synthesized on a solid substrate, such as plastic pins or some other surface. The test compounds are reacted with GLUT10, or fragments thereof, and washed. Bound GLUT10 is then detected by methods well known in the art. Purified GLUT10 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GLUT10 specifically compete with a test compound for binding GLUT10. In this manner, the antibodies can be used to detect the presence of any peptide that shares one or more antigenic determinants with GLUT10.

Novel binding agents found in such screening methods include non-natural binding agents, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like.

The term "agent" as used herein describes any molecule, e.g. protein, oligopeptide, small organic molecule, polysaccharide, polynucleotide, etc. with the capability of directly or indirectly altering cell surface receptor internalization in response to ligand binding. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Exemplary GLUT10 inhibitors known by those skilled in the art to inhibit glucose transporters, include but are not limited to D-glucose, D-fructose, Cytochalasin B, and maltose.

Where the screening assay is a binding assay, one or more of the molecules may be joined to a label, where the label can directly or indirectly provide a detectable signal. Various labels include radioisotopes, fluorescers, chemiluminescers, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures.

Where the screening assay is a translocation assay, the GLUT 10 gene expressed in a host cell may be fused to a gene encoding a detectable group such as a green fluorescent protein, so that movement (translocation) of the encoded glucose transporter within the cell in response to direct binding of the compound being screened to the encoded protein, or indirect action of the compound being screened through activity on other cell constituents that participate in translocation, may be determined. Such techniques are known to those skilled in the art and are described, for example, in U.S. Pat. No. 5,891,646 to Barak et al., the disclosure of which is incorporated herein by reference in its entirety.

A variety of other reagents may be included in the screening assay. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc. may be used.

The mixture of components may be added in any order that provides for the requisite binding. Incubations may be performed at any temperature which facilitates optimal activity, typically between 4 and 40° C. Incubation periods are selected for optimum activity, but may also be optimized to facilitate rapid high-throughput screening. Typically between 0.1 and 1 hour will be sufficient.

Compounds with pharmacological activity are able to enhance or interfere with the internalization of cell surface receptors in response to ligand binding. Binding to the site on the receptor corresponding to the subject oligopeptides is indicative of such activity, as is the ability to interfere with the binding of the subject oligopeptides to the cognate receptor. The compounds having the desired pharmacological activity may be administered in a physiologically acceptable carrier to a host, as previously described. The inhibitory agents may be administered in a variety of ways, orally, parenterally e.g. subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

In additional embodiments, the nucleotide sequences which encode GLUT10 may be used in any molecular biology techniques that have yet to be developed, provided the new techniques rely on properties of nucleotide sequences that are currently known, including, but not limited to, such properties as the triplet genetic code and specific base pair interactions.

The examples, which follow, are set forth to illustrate the present invention, and are not to be construed as limiting thereof. In the following examples, BAC means bacterial artificial chromosome; 2-DOG means 2-deoxy-D-glucose; EST means expressed sequence tag; GLUT means glucose transporter; MBS means modified Barth's saline; RACE means rapid amplification of cDNA ends; RT-PCR means reverse transcriptase-polymerase chain reaction; TMD means transmembrane domain; YAC means yeast artificial chromosome; Mb means Megabase; mM means millimolar; mg means milligram; ml means milliliter; nl means nanoliter; $\mu$g means microgram; $\mu$l means microliter; U means units; 1 means liter; 1M means micromolar; $^3$H means tritium; Ci means Curies; mmol means millimole; bp means base pair; Da means Dalton; kb means kilobase pair; aa means amino acid; pmol means picomol; min means minute; and all temperatures, unless otherwise indicated, are in degrees Celsius.

EXAMPLE 1

Cloning and Localization of GLUT10

Materials and Methods. Analysis of published human sequence data produced by the Human Chromosome 20 Sequencing Group at the Sanger Centre (ftp://ftp.sanger.ac.uk/pub/human/sequences/Chr 20/) identified a partial transcript described as a "membrane transporter-like protein" (Genbank# AL031055). This sequence was used in homology searches (Altschul, et al. (1990) *J Mol Biol* 215, 403–410) of the non-redundant nucleotide and EST databases at NCBI (http://www.ncbi.nlm.nih.gov/). Primers (GLUT10 #11,12) designed from this sequence were used to amplify a full-length GLUT10 transcript from Marathon-Ready™ human placental cDNA using the Advantage™ cDNA PCR and 5'/3' RACE Adapter kits (Clontech Laboratories). All amplified products were sequenced bi-directionally on an ABI Prism 377 automated DNA sequencer (Applied Biosystems) by the Wake Forest University School of Medicine DNA Sequencing Core Laboratory. PCR primers specific for GLUT10 (GLUT10 #2, 4) were used to screen a panel of overlapping Human YAC library and CITB BAC library clones (Version 4.0, Research Genetics) that span a contiguous 7 Mb region of human chromosome 20q12-13.1 (Price, et al. (1999) *Genomics* 62, 208–215). The localization of GLUT10 was inferred from the retention pattern within individual BAC clones.

Chromosomal Localization of GLUT10. Significant evidence of association with Type 2 diabetes was identified with two genetic markers on human chromosome 20, ADA and D20S888 (Price, et al. (1997) *Am. J. Hum. Genet.* 58 (suppl.), A241). A critical survey of the published human sequence data in this region identified a partial transcript with similarity to membrane transport proteins within the annotated BAC clone 28H20 (Genbank# AL031055). Specific PCR primer sets were then designed to locate this transcript sequence within a contiguous 7 Mb physical map of overlapping BAC clones spanning the two linkage disequilibrium maxima of the chromosome 20 Type 2 diabetes susceptibility region. The membrane transporter-like transcript was mapped approximately 100 kb telomeric to the genetic marker D20S888.

Genomic Structure and Sequence Analysis. 5' and 3' RACE was performed using primer sets specific for the membrane transporter-like transcript and human placental mRNA to isolate the full-length 4384 bp cDNA (SEQ ID NO:1). The GLUT10 cDNA encodes a 541 amino acid protein (SEQ ID NO:2) with a calculated molecular mass of 56,875 Da. The predicted initiator methionine lies within an appropriate consensus for initiation of translation (Kozak. (1987) *Nucleic Acids Res.* 15, 8125–8148) and is preceded by a 250 bp 5' untranslated region with numerous in-frame stop codons. The 1626 bp coding sequence is followed by a 2491 bp 3' untranslated sequence that extended to the poly(A) tail. The 3' sequence of the cDNA matched UniGene cluster Hs178603 that had been mapped to chromosome 20 between genetic markers D20S119 and D20S197. The complete cDNA sequence was submitted to both GenBank and HUGO and assigned the approved gene symbol SLC2A10, alias GLUT10 (GenBank# AF248053). The GLUT10 cDNA sequence was aligned with the genomic DNA of human BAC clone 281120 (GenBank# AL031055) to reveal the gene organization (FIG. 1A). The size and sequence of the GLUT10 exons were also confirmed through multiple RT-PCR and RACE experiments as well as alignments with existing EST clones (e.g. GenBank# BE237601, AA313045, AW028359, AA628914, WO2942). The GLUT10 gene is organized in 5 exons spanning 26.8 kb of genomic DNA (FIG. 1A). The size of each exon and intron, the sequence at the exon/intron junctions, and the amino acid interrupted at each junction are indicated (FIG. 1B). Exon one codes only for the initiating methionine and the first base of the second codon, and is followed by an unusually large second exon. Exons 2–5 encompass the remaining coding sequence (amino acids 2 to 541), and exon 5 also encodes a long 3' untranslated region of 2491 bp.

Searches (Altschul, et al. (1990) *J Mol Biol* 215, 403–410) of the non-redundant nucleotide and EST databases at NCBI (http://www.ncbi.nlm.nih.gov/) revealed significant homology between the GLUT10 cDNA and both bacterial and mammalian hexose transporters. The predicted amino acid sequence of GLUT10 is nearly identical in length to the very recently published GLUT9 homologue (541 aa vs 540 aa), but ranges from 3% (GLUT2; 524 aa) to 13% (GLUT8; 477 aa) longer than other known members of the human GLUTn family (n=1–5, 8). Pairwise global alignment (GCG gap program, gap=10, extension=2) revealed that GLUT10 shares from 30% (GLUT1) to 33% (GLUT8) identity with the previously identified human GLUTn (n=1–5,8). A human GLUTn family multiple sequence alignment and the predicted transmembrane domain (TMD) organization for GLUT10 are shown in FIG. 2A. The hypothetical TMD structure was analyzed using two newer Hidden Markov Model (HMM) programs, HMMTOP (Tusnády and Simon. (1998) *J. Mol. Biol.* 283, 489–506) and TMHMM (Sonnhammer, et al. (1998) *Proc. of Sixth Int. Conf. on Intelligent Systems for Molecular Biology*, pp. 175–182, Glasgow J., Littlejohn, T., Major, F., Lathrop, R., Sankoff, D., & Sensen C. Menlo Park, Calif.: AAAI Press), and compared with the older TMPRED (Hofmann and Stoffel. (1993) *Biol. Chem. Hoppe-Seyler* 374, 166). The HMM programs were in excellent agreement and predict the signature 12 TMD structure while TMPRED predicted only 9 TMD. The additional residues in GLUT10 are found in the longer exofacial loop 9 between TMD9 and TMD10 (91 aa), as compared to the loops for GLUT1 (8 aa), GLUT8 (33 aa), and GLUT9 (11 aa) predicted by HMM.

Figure 2B:
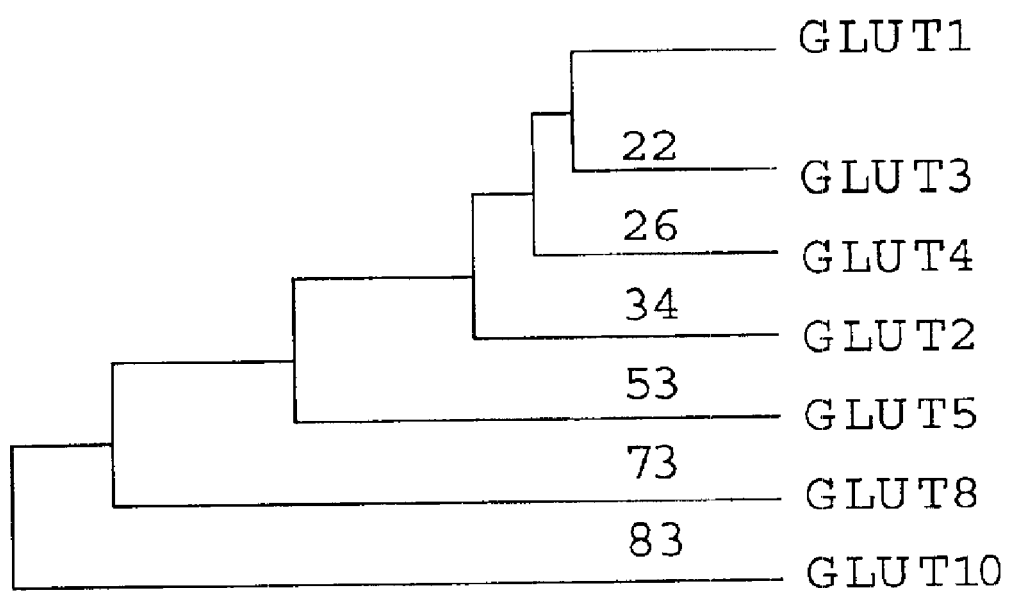
FIG. 2B depicts the approximate phylogram of the GLUT family. Annotated distances are in substitutions per 100 residues. The unrooted phylogram was generated using the GCG distances program under a Kimura protein substitution model from the FIG. 2A multiple sequence alignment, and reconstructed using a UPGMA method. The sequences used are SwissProt Accession Nos. P 11166 (GLUT1, SEQ ID NO: 38), P11168 (GLUT2, SEQ ID NO: 39), P11169 (GLUT3. SEQ ID NO: 40), P14672 (GLUT4, SEQ ID NO: 41), P22732 (GLUT5, SEQ ID NO: 42), and EMBL Translation No. CAB89809 (GLUT8, SEQ ID NO: 43).

GLUT10 retains several sequence motifs characteristic of the mammalian glucose transporters including ProGluThr{Arg,Gly}Lys in loop 12, GlyArg{Arg,Lys} between TMD2 and 3, {Glu,Asp}ArgAlaGlyArgArg between TMD9 and 10, GlnGlnLeu{Ser,Thr}Gly in TMD7, and tryptophan residues (Trp430 and Trp454), in TMD10 and 11 that correspond to Trp388 and Trp412 of GLUT1. These tryptophan residues have previously been implicated in GLUT1 cytochalasin B binding and hexose transport (Mueckler. (1994) *Eur. J. Biochem.* 219, 713–725). Sites for N-linked glycosylation are predicted at residue 332 between TM8 and TM9, and residue 526 in the cytoplasmic carboxyl terminus. The GLUT10 loop 9 sequence does not exhibit significant homology to existing protein or nucleotide databases, nor obvious tandem or inverted repeat structure. All three *C. elegans* and *A. thaliana* proteins (582–639 aa) demonstrate weak homology in the putative 91 residue TMD9 plus loop 9 region, while the shorter (457 aa) bacterial homologues lack this region, suggesting further mutation events in this region after eukaryotic divergence. FIG. 2B shows a phylogram for the human GLUTn family that quantifies the distinction of GLUT10 from the rest of the transporters. GLUT10 is evolutionarily more distant from n=1–5,8 than any other pair of the family and most similar to the recently identified GLUT8. GLUT3 and GLUT1 are predicted to be closest in distance, but the difference between GLUT1/GLUT3 and GLUT1/GLUT4 is small enough to be affected by relatively small changes to the sequence alignment. This simple model broadly supports previous alignments for this family of hexose transporters (Doege, et al. (2000) *J. Biol. Chem.* 275, 16275–80). As expected, BLAST searches also revealed high-scoring homologues in other organisms: *C. elegans* (PIR:T27072, T27077, T23658 hypothetical proteins Y51A2D.4, Y51A2D.5, M01F1.5) approximately 22% global identity; *A. thaliana* (PIR:E70070, hypothetical protein) 25% identity; *B. subtilis* (PIR:E70070, Metabolite transport ywtG) 20% identity; *L. brevis* (accession AF045552, D-xylose transporter) 22% identity.

EXAMPLE 2

Tissue Expression Analysis

Material and Methods. A poly (A) RNA Multiple Tissue Northern blot (catalog number 7760–1) was purchased from Clontech Laboratories and hybridization was carried out according to manufacturer's recommendations. PCR amplification was conducted using GLUT10 primers 3 and 17 to screen 24 tissues in the Rapid-Scan™ Gene Expression Panel (OriGene Technologies, Inc) according to manufacturer's guidelines.

Results. The GLUT10 cDNA was used to probe a poly(A) RNA Multiple Tissue Northern Blot. A single 4.4 kb transcript was detected in all tissues examined, with levels highest in heart, lung>liver, skeletal muscle, pancreas>brain, placenta>kidney (FIG. 3A). A more extensive tissue expression survey was carried out using RT-PCR analysis. PCR was performed using first-strand cDNA prepared from 24 human tissues and oligonucleotide primers specific for GLUT10 or actin as a control. As shown in FIG. 3B, GLUT 0 mRNA was readily detected in liver, lung, placenta, salivary gland, thyroid, adrenal, pancreas, ovary, prostate, and skin. This widespread distribution of GLUT10 mRNA was also observed in a search of existing ESTs. The 3' end of the GLUT10 cDNA matches the UniGene cluster Hs178603 that is represented by 44 ESTs from various tissue libraries including aorta (1 EST), bone (3 ESTs), brain (1 EST), foreskin (4 ESTs), heart (2 ESTs), parathyroid (6 ESTs), prostate (1 EST), testis (1 EST), uterus (8 ESTs), and whole embryo (3 ESTs). In searching the EST database, several other representative ESTs were also identified from liver, kidney, lung, pancreas, neuron, fetal brain, fetal heart, fetal liver, and fetal lung libraries.

EXAMPLE 3

Functional Analysis of Wild Type GLUT10 in *Xenopus* Oocytes

Material and Methods. A full-length GLUT10 cDNA was cloned into the expression vector pCMV-Tag4a (Stratagene). A PCR-based strategy employing Pfu polymerase was used for site-directed mutagenesis to generate the GLUT10 single nucleotide polymorpisms. The PCR products were digested with Eco RI, subcloned into pCMV-Tag4a, and the complete insert was sequenced to confirm the identity of the A206T and A287T GLUT10 glucose transporter cDNAs. The pcDNA3.1/GS plasmids expressing the full-length GLUT3 and GLUT4 cDNA were purchased from Invitrogen Corporation. Capped mRNA was generated using the mMES-SAGE mMACHINE™ transcription kit (Ambion Inc).

Adult female *Xenopus laevis* were obtained from Xenopus Express (Homosassa, Fla.) and housed at 17–19° C. on a twelve-hour light/dark cycle. Stage V-VI oocytes were removed from anesthetized frogs and placed in isolation media (108 mM NaCl, 1 mM EDTA, 2 mM KCl, 10 mM HEPES, pH 7.5). The oocyte follicular layer was removed by immersion in 0.5 mg/ml collagenase buffer (83 mM NaCl, 2 mM KCl, 1 mM $MgCl_2$, and 5 mM HEPES, pH 7.5). Isolated oocytes were maintained in modified Barth's saline (MBS; 88 mM NaCl, 1 mM KCl, 10 mM HEPES, 0.82 mM $MgSO_4$, 2.4 mM $NaHCO_3$, 0.91 mM $CaCl_2$, and 0.33 mM $Ca(NO_3)_2$, pH 7.5). Visually healthy oocytes were injected with 30 nl of either a mRNA solution (1.0 μg/μl) or sterile water at the interface between the animal and vegetal poles. Individual oocytes were placed in 96-well microtiter plates (Costar Corporation) containing MBS plus 2 mM sodium pyruvate, 0.5 mM theophylline, 10 U/ml penicillin, 10 mg/l streptomycin and 50 mg/] gentamycin (Sigma) at 22° C.

2-Deoxy-D-glucose (2-DOG) uptake assays were performed at 22° C. using pools of 4 to 12 healthy oocytes 3 days post injection. Oocyte pools were washed in MBS, and incubated for 30 min at 22° C. in 100 μl MBS in the presence of 25 or 250 μM 2-DOG [1,2-³H] DOG (final specific activity=0.5 Ci/mmol) (NEN Life Science Products, Inc.; American Radiochemical Company). Competitors, inhibitors, or insulin were added to the incubation as indicated. Uptake was terminated by removal of the radioactive solution and three 500 μl washes with ice-cold MBS containing 0.1 mM phloretin (Sigma). Pools of oocytes were dissolved in 10% SDS, mixed with scintillation fluid, and internalized radioactivity was measured by scintillation spectrometry using a Beckman LS-600 scintillation counter. Data are expressed as the arithmetic mean or median of duplicate or triplicate pools of 4 to 12 oocytes at each data point. Transport kinetics were analyzed by best-fit analysis of data points (Cricket Graph, Computer Associates) and Eadie-Hofstee transformation.

Figure 4:
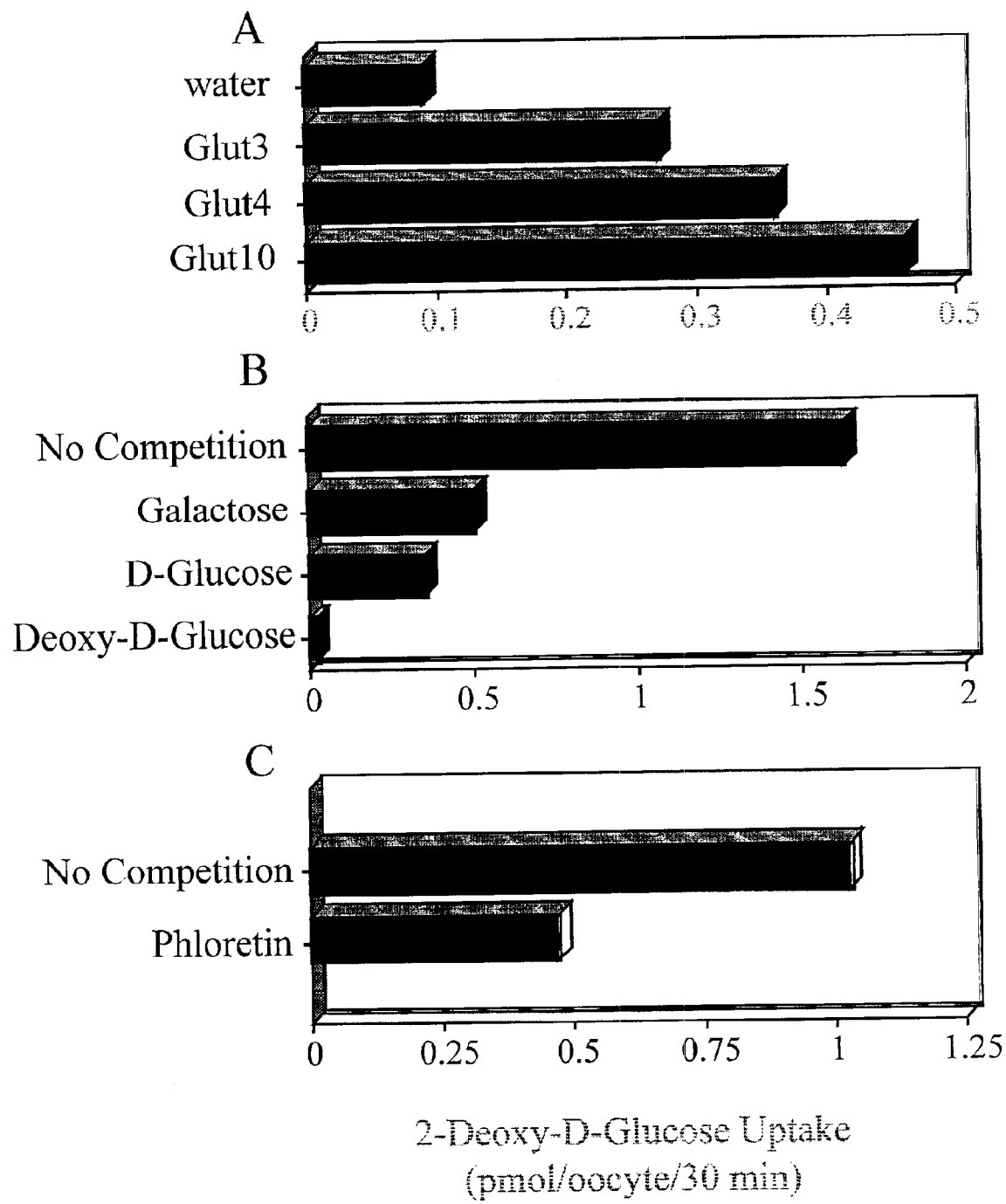
FIG. 4 shows GLUT10 mediated 2-DOG uptake in Xenopus oocytes. (A) Uptake of 2-DOG (25 $\mu$M, 30 min at 22° C.) was measured 3 days after injection of water, or 30 ng of GLUT3, GLUT4, or GLUT10 RNA into Xenopus oocytes. Each bar represents the mean of duplicate determinations using 10 oocytes per assay. (B) Effect of competitors on 2-DOG uptake. Xenopus oocytes injected with GLUT10 RNA (30 ng) or water were incubated for 30 nin at 22° C. with 250 $\mu$M of [$^3$H]2-DOG in the presence of 25 mM 2-DOG, D-glucose, or D-galactose. (C) Effect of phloretin on 2-DOG uptake. Xenopus oocytes injected with GLUT10 RNA (30 ng) or water were incubated for 30 min at 22° C. with 25 $\mu$M of [$^3$H]2-DOG in the presence of 100 $\mu$M phloretin.
Figure 5:
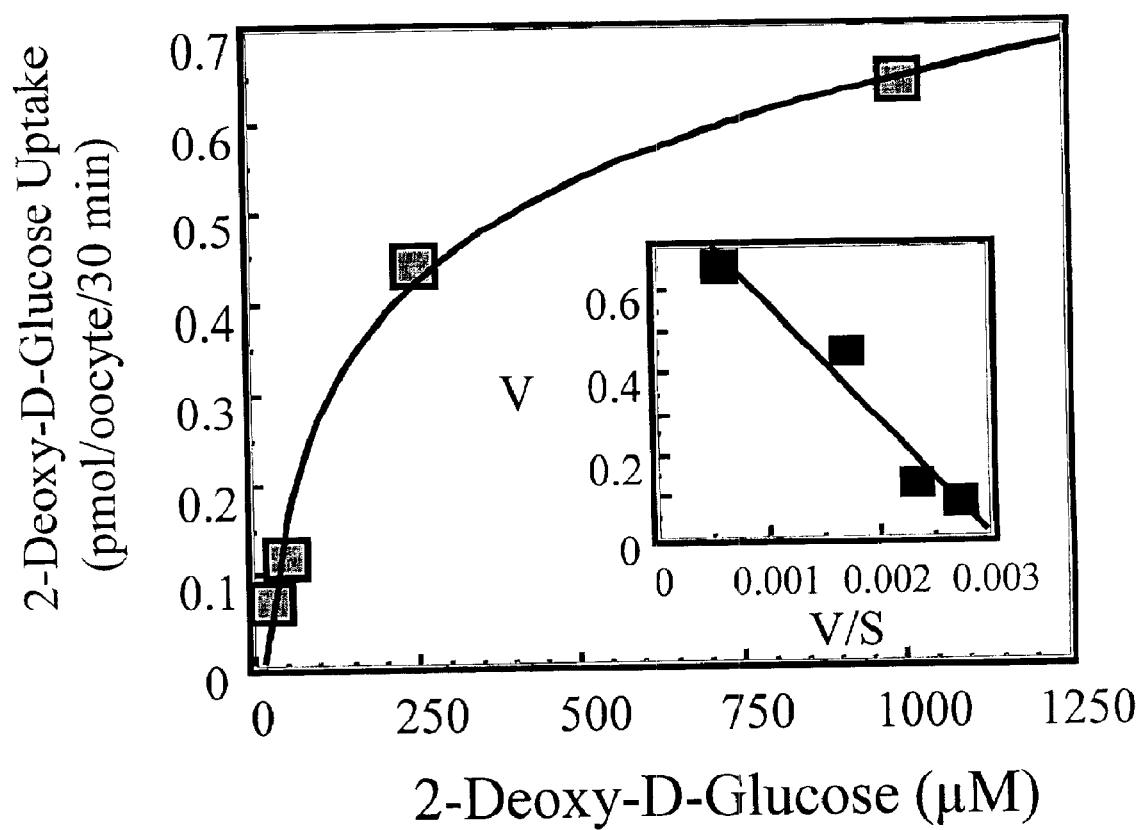
FIG. 5 shows the concentration response curve for 2-DOG uptake. Xenopus oocytes injected with GLUT10 RNA (30 ng) or water were incubated with the indicated concentration of [$^3$H]2-DOG for 30 min at 22° C. The oocytes were washed and lysed to determine associated radioactivity. Each point represents the average of 4 to 10 oocytes. The uptake values were corrected for the background uptake in water-injected oocytes. Inset, Eadie-Hofstee analysis of uptake data revealed an apparent $K_m$ for 2-DOG uptake of 280 $\mu$M and a $V_{max}$ of 0.85 pmol oocyte$^{-1}$ 30 min$^{-1}$.

Results. The *Xenopus laevis* oocyte expression system was used to determine whether GLUT10 is a functional glucose transporter. Capped mRNA were transcribed from the full-length human GLUT3, GLUT4, or GLUT10 cDNA and used to inject *Xenopus* oocytes. FIG. 4A shows the 2-DOG transport mediated by GLUT10 with respect to human GLUT3 and GLUT4. GLUT10-injected oocytes exhibited 2-DOG uptake that was 5-fold over the water-injected controls and was similar to the uptake in GLUT3 and GLUT4-injected oocytes. As shown in FIG. 4B, a 100-fold excess of either 2-DOG or D-glucose effectively competed with radioactive 2-DOG for uptake. D-galactose also inhibited 2-DOG uptake but less effectively. In contrast, a 100-fold excess of fructose did not inhibit 2-DOG uptake (data not shown). Glucose uptake was also inhibited by phloretin (FIG. 4C), a general inhibitor of mammalian glucose transporters. To determine the affinity of GLUT10 for glucose, GLUT10 mRNA-injected oocytes were incubated for 30 min with increasing concentrations of [³H]2-DOG. Preliminary studies had shown that transport of 25 μM [³H]2-DOG was linear with time for up to 60 min at 22° C. (data not shown). The transport of [³H]2-DOG by GLUT10 mRNA-injected oocytes was saturable and of relatively high affinity (FIG. 5). As determined by Eadie-Hofstee analysis (FIG. 5, inset), GLUT10 mediated 2-DOG uptake with an apparent $K_m$ of approximately 0.3 mM and a $V_{max}$ of 0.85 pmol oocyte$^{-1}$ 30 min$^{-1}$.

Figure 6:
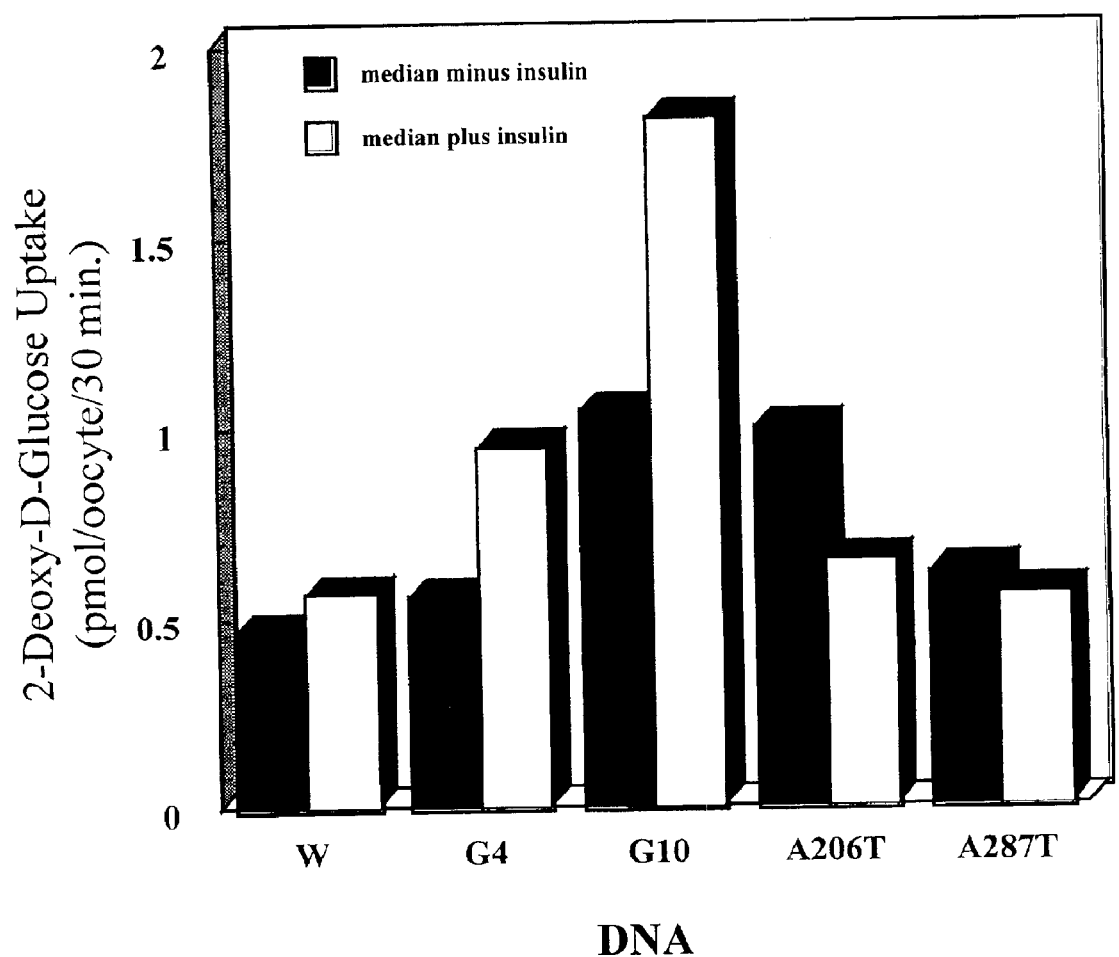
FIG. 6 shows insulin-stimulation of 2-DOG uptake in GLUT10-injected oocytes. Uptake of 2-DOG was measured 3 days after injection of water, or 30 ng of GLUT4 or wild type and isoforms of GLUT10 RNA into Xenopus oocytes. Following a preincubation in the presence or absence of 100 $\mu$M insulin for 30 min at 22° C., the oocyte pools were incubated with 250 $\mu$M [$^3$H]2-DOG for 30 min in the presence or absence of 100 [M insulin. Each bar represents the median of triplicate determinations using pools of 6 to 10 oocytes per assay.

GLUT10 mRNA-injected oocytes exhibited a low but reproducible level of 2-DOG uptake activity. This activity is similar to that exhibited by GLUT4 in the absence of insulin (Rumsey, et al. (2000) *J Biol Chem*). In order to determine if GLUT10, like GLUT4, activity is stimulated by insulin, GLUT10-injected oocytes were incubated in the presence or absence of insulin prior to measuring 2-DOG uptake activity. As shown in FIG. 6, pre-incubation of oocytes with 100 μM insulin for 30 min stimulated 2-DOG transport by GLUT4 as well as the wild type GLUT10.

EXAMPLE 4

SNPs Associated with the Diabetes

Because GLUT10 was localized within the type 2 diabetes-linked region of chromosome 20q12-13.1, and encoded a potential glucose transporter, the coding sequence for allelic variants that may contribute to increased type 2 diabetes susceptibility were evaluated. Single-stranded conformational polymorphism (SSCP) analysis was used to screen each identified exon in 235 unrelated Caucasian type 2 diabetic and 100 Caucasian unrelated non-diabetic control subjects for potential coding changes. Oligonucleotide nucleotide primer pairs were designed for the proximal 5' promoter (covering 450 nucleotides upstream from the transcription start site) and 3' untranslated regions (covering 250 nucleotides downstream from the transcription stop site), and to flank each of the predicted exons (Table 1). Six primer sets were constructed for exon 2, the largest exon (1284 bp).

TABLE 1

| Oligonucleotide | Sequence (and SEQ ID NO:__) | Location |
|---|---|---|
| GLUT10 5' P1F | GGCACCTCTTCCCTGCAAAG (3) | −(157–138)[a] |
| GLUT10 5' P1R | CCCTCCCGCGCGCAGCGCCG (4) | 121–102[b] |
| GLUT10 5' P2F | CGTCCCGCCTCCAGGCCT (5) | 55–72[b] |
| GLUT10 5' P2R | CCATGGCGAGCGGGACT (6) | 254–238[b] |
| GLUT10 ex1F | CGTCCCGCCTCCAGGCCT (7) | 132–149[b] |
| GLUT10 ex1R | GGCGGTGTCTACACCCTGG (8) | +(63–46)[c] |
| GLUT10 ex2aF | TGACAGATGGAGGGAAGGTTG (9) | −(52–33)[c] |
| GLUT10 ex2aR | AGGAGCAGGCTGCCCACCA (10) | 417–399[b] |
| GLUT10 ex2bF | CTGGCAGTCATATCAGGTGC (11) | 326–345[b] |
| GLUT10 ex2bR | AATGGCGAAGCCAACCACAG (12) | 586–567[b] |
| GLUT10 ex2cF | GGAGCAACTTGGTGCTGCTG (13) | 489–508[b] |
| GLUT10 ex2cR | AGTGGCCCAGCCGAACATGT (14) | 766–747[b] |
| GLUT10 ex2dF | CTCAACTATGCACTGGCTGG (15) | 707–726[b] |
| GLUT10 ex2dR | CGGAGCTGAAGATGGTGGAG (16) | 1031–1012[b] |
| GLUT10 ex2eF | CTCTTCCAGCAACTAACAGGG (17) | 968–988[b] |
| GLUT10 ex2eR | AGCTTGGGCCTGAGTCCATG (18) | 1235–1216[b] |
| GLUT10 ex2fF | AGTGGCATAGGCCTCGTCAG (19) | 1184–1203[b] |
| GLUT10 ex2fR | AGAAGTCTCCAGAGTCACCTG (20) | +(97–76)[c] |
| GLUT10 ex3F | GGCTGCATGTTTGACCTGATG (21) | −(45–026)[c] |
| GLUT10 ex3R | GCTTTAGAGTAGGGAGCTTGG (22) | +(62–43)[c] |
| GLUT10 ex4F | TGACCTAGAACCTACCAGTTG (23) | −(53–34)[c] |
| GLUT10 ex4R | TCCTGAAGCTGTGTGCTTGG (24) | +(76–56)[c] |
| GLUT10 ex5F | GGGAACCCCAGTGGAAGGT (25) | −(84–65)[c] |
| GLUT10 ex5R | CAGGCAGACGGATTCCTCAG (26) | 1892–1873[b] |
| GLUT10 3' #1F | AACTCCACTGGCATCCCGT (27) | 1866–1844[b] |
| GLUT10 3' #1R | CATGAAACTAGATCCTCAAG (28) | 2100–2081[b] |

[a]Numbers indicate oligonucleotide position relative to transcriptional start site
[b]Numbers indicate location within cDNA
[c]Numbers in parentheses refer to oligonucleotide position relative to intron/exon junction; − (numbers) indicate position relative to acceptor side of exon, + (numbers) indicate position relative to donor side of exon Single-strand conformational polymorphism (SSCP) analysis detected mobility shifts in two primers sets used to evaluate different regions of exon 2 (2D and 2E). DNA sequence content of PCR products with different mobility patterns was verified using a Big Dye Terminator Cycle Sequencing Kit and DNA Sequencer model 377 (PE/Applied Biosystems, Foster City, Calif.). Two single nucleotide polymorphisms (SNPs) were identified within exon 2. The first polymorphism (SNP1) is a guanine to adenosine transition at base pair 616 (G616A) of the GLUT10 coding sequence (the A residue in the initiator ATG is base pair+1). A total of 236 unrelated Type 2 diabetes patient DNA samples and 100 control DNA samples were tested for the presence of the G616A polymorphic sequence. G616A is present in 8% of chromosomes from Caucasian type II diabetics and 2% of chromosomes from control subjects (Table 2). No G616A (SNP1 A/A) homozygotes were detected. Statistical analysis of the allelic distribution observed in the two population groups using chi square tests indicated that the difference in frequencies approaches significance, with a calculated p-value of 0.06. The SNP1 G/A transition at base pair 616 leads to an alanine to threonine substitution at amino acid position 206. This substitution occurs in the loop between predicted transmembrane domains six and seven. The second polymorphism, SNP2, is also a guanine to adenosine transition, at base pair 859 (G859A) of the GLUT10 coding sequence. This polymorphism was detected in 2 chromosomes in heterozygous Caucasian type 2 diabetics out of 236 patient DNAs that were tested and was not observed in 100 control DNA samples. The SNP2 G-A transition results in an alanine to threonine substitution at amino acid position 287. This substitution occurs near the end of the seventh predicted transmembrane domain. A Thr110Ile substitution in the second predicted transmembrane domain of GLUT2 did not have functional consequences, but a highly conservative Val197Iso amino acid change in the fifth predicted transmembrane domain of GLUT2 was shown to completely abolish glucose transport activity in *Xenopus* oocytes (Mueckler, et al. (1994) *J Biol Chem* 27; 17765–17767).

TABLE 2

| Allele | Caucasian Controls (n = 96) | Caucasian Diabetics (n = 236) |
|---|---|---|
| G | 0.98 | 0.92 |
| A | 0.02 | 0.08 |

EXAMPLE 5

Functional Analysis of Allelic Variants of GLUT10 in *Xenopus* Oocytes

To evaluate the functional consequences of these allelic variants, GLUT10 homozygous SNP1 and SNP2 constructs were generated using site-directed mutagenesis. Each construct was expressed in *Xenopus* oocytes, and different aspects of glucose transport were measured. Initial studies indicate that the glucose transport activity of the SNP constructs is not significantly different from wild type GLUT10. In contrast to wild type GLUT10, the 2-DOG uptake activity of the GLUT10 A206T and A28T isoforms was not stimulated by pre-incubation with insulin (FIG. 6).

Impaired insulin-stimulated glucose transport has been implicated as the mechanism responsible for the reduced rate of insulin-stimulated muscle glycogen synthesis in patients with type 2 diabetes. The finding of insulin-insensitive GLUT10 isoforms enriched in the type 2 diabetic population provides a potential mechanism for the impaired insulin-stimulated glucose transport in these patients.

The foregoing examples are illustrative of the present invention, and are not to be construed as limiting thereof. The invention is described by the following claims, with equivalents of the claims to be included therein.

What is claimed is:

1. An isolated nucleic acid encoding a glucose transporter protein comprising the amino acid sequence as set forth in SEQ ID NO: 2.

2. The isolated nucleic acid according to claim 1 comprising the nucleotide sequence as set forth in SEQ ID NO: 1.

3. An isolated host cell transformed with the isolated nucleic acid according to claim 1.

4. A recombinant nucleic acid molecule comprising a promoter operatively associated with the isolated nucleic acid according to claim 1.

5. An isolated host cell containing the recombinant nucleic acid according to claim 4.

6. The isolated host cell according to claim 5, wherein said host cell expresses said glucose transporter protein.

* * * * *

UNITED STATES PATENT AND TRADEMARK OFFICE
CERTIFICATE OF CORRECTION

PATENT NO. : 6,849,728 B1
DATED : February 1, 2005
INVENTOR(S) : Bowden et al.

Page 1 of 1

It is certified that error appears in the above-identified patent and that said Letters Patent is hereby corrected as shown below:

<u>Column 4,</u>
Line 67, should read -- presence or absence of 100 $\mu$M insulin. Each bar represents --

Signed and Sealed this

Seventh Day of June, 2005

JON W. DUDAS
*Director of the United States Patent and Trademark Office*

SEQUENCE LISTING

```
<160> NUMBER OF SEQ ID NOS: 43

<210> SEQ ID NO 1
<211> LENGTH: 4395
<212> TYPE: DNA
<213> ORGANISM: Homo sapiens
<220> FEATURE:
<221> NAME/KEY: CDS
<222> LOCATION: (250)..(1875)

<400> SEQUENCE: 1 gaggggtcc ttgccaggcc tggggcggcc ggggcggtc ctgggctccc ctccgtcccg      60
cctccaggcc tcggggcctg gctggccgac gtggcgttgg cggcgctgcg cgcgggaggg     120
cagggcagga gggacagagg cggggcggg ccggaaagtt tgtccggcgg cagcggcgtt     180
ggggactccg gcgggggatg cgcgcccggc ccctcagcgc ccccagcacg ccgccgagtc     240 ccgctcgcc atg ggc cac tcc cca cct gtc ctg cct ttg tgt gcc tct gtg    291
        Met Gly His Ser Pro Pro Val Leu Pro Leu Cys Ala Ser Val
        1               5                   10 tct ttg ctg ggt ggc ctg acc ttt ggt tat gaa ctg gca gtc ata tca      339
Ser Leu Leu Gly Gly Leu Thr Phe Gly Tyr Glu Leu Ala Val Ile Ser
 15                  20                  25                  30 ggt gcc ctg ctg cca ctg cag ctt gac ttt ggg cta agc tgc ttg gag      387
Gly Ala Leu Leu Pro Leu Gln Leu Asp Phe Gly Leu Ser Cys Leu Glu
                 35                  40                  45 cag gag ttc ctg gtg ggc agc ctg ctc ctg ggg gct ctc ctc gcc tcc      435
Gln Glu Phe Leu Val Gly Ser Leu Leu Leu Gly Ala Leu Leu Ala Ser
             50                  55                  60 ctg gtt ggt ggc ttc ctc att gac tgc tat ggc agg aag caa gcc atc      483
Leu Val Gly Gly Phe Leu Ile Asp Cys Tyr Gly Arg Lys Gln Ala Ile
         65                  70                  75 ctc ggg agc aac ttg gtg ctg ctg gca ggc agc ctg acc ctg ggc ctg      531
Leu Gly Ser Asn Leu Val Leu Leu Ala Gly Ser Leu Thr Leu Gly Leu
     80                  85                  90
```

-continued

| | | |
|---|---|---|
| gct ggt tcc ctg gcc tgg ctg gtc ctg ggc cgc gct gtg gtt ggc ttc<br>Ala Gly Ser Leu Ala Trp Leu Val Leu Gly Arg Ala Val Val Gly Phe<br>95                        100                      105                    110 | 579 |
| gcc att tcc ctc tcc tcc atg gct tgc tgt atc tac gtg tca gag ctg<br>Ala Ile Ser Leu Ser Ser Met Ala Cys Cys Ile Tyr Val Ser Glu Leu<br>115                      120                      125 | 627 |
| gtg ggg cca cgg cag cgg gga gtg ctg gtg tcc ctc tat gag gca ggc<br>Val Gly Pro Arg Gln Arg Gly Val Leu Val Ser Leu Tyr Glu Ala Gly<br>130                      135                      140 | 675 |
| atc acc gtg ggc atc ctg ctc tcc tat gcc ctc aac tat gca ctg gct<br>Ile Thr Val Gly Ile Leu Leu Ser Tyr Ala Leu Asn Tyr Ala Leu Ala<br>145                      150                      155 | 723 |
| ggt acc ccc tgg gga tgg agg cac atg ttc ggc tgg gcc act gca cct<br>Gly Thr Pro Trp Gly Trp Arg His Met Phe Gly Trp Ala Thr Ala Pro<br>160                      165                      170 | 771 |
| gct gtc ctg caa tcc ctc agc ctc ctc ttc ctc cct gct ggt aca gat<br>Ala Val Leu Gln Ser Leu Ser Leu Leu Phe Leu Pro Ala Gly Thr Asp<br>175                      180                      190 | 819 |
| gag act gca aca cac aag gac ctc atc cca ctc cag gga ggt gag gcc<br>Glu Thr Ala Thr His Lys Asp Leu Ile Pro Leu Gln Gly Gly Glu Ala<br>                    195                      200                    205 | 867 |
| ccc aag ctg ggc ccg ggg agg cca cgg tac tcc ttt ctg gac ctc ttc<br>Pro Lys Leu Gly Pro Gly Arg Pro Arg Tyr Ser Phe Leu Asp Leu Phe<br>           210                      215                    220 | 915 |
| agg gca cgc gat aac atg cga ggc cgg acc aca gtg ggc ctg ggg ctg<br>Arg Ala Arg Asp Asn Met Arg Gly Arg Thr Thr Val Gly Leu Gly Leu<br>225                      230                      235 | 963 |
| gtg ctc ttc cag caa cta aca ggg cag ccc aac gtg ctg tgc tat gcc<br>Val Leu Phe Gln Gln Leu Thr Gly Gln Pro Asn Val Leu Cys Tyr Ala<br>240                      245                      250 | 1011 |
| tcc acc atc ttc agc tcc gtt ggt ttc cat ggg gga tcc tca gcc gtg<br>Ser Thr Ile Phe Ser Ser Val Gly Phe His Gly Gly Ser Ser Ala Val<br>255                      260                      265                    270 | 1059 |
| ctg gcc tct gtg ggg ctt ggc gca gtg aag gtg gca gct acc ctg acc<br>Leu Ala Ser Val Gly Leu Gly Ala Val Lys Val Ala Ala Thr Leu Thr<br>                    275                      280                    285 | 1107 |
| gcc atg ggg ctg gtg gac cgt gca ggc cgc agg gct ctg ttg cta gct<br>Ala Met Gly Leu Val Asp Arg Ala Gly Arg Arg Ala Leu Leu Leu Ala<br>                    290                      295                    300 | 1155 |
| ggc tgt gcc ctc atg gcc ctg tcc gtc agt ggc ata ggc ctc gtc agc<br>Gly Cys Ala Leu Met Ala Leu Ser Val Ser Gly Ile Gly Leu Val Ser<br>           305                      310                    315 | 1203 |
| ttt gcc gtg ccc atg gac tca ggc cca agc tgt ctg gct gtg ccc aat<br>Phe Ala Val Pro Met Asp Ser Gly Pro Ser Cys Leu Ala Val Pro Asn<br>320                      325                      330 | 1251 |
| gcc acc ggg cag aca ggc ctc cct gga gac tct ggc ctg ctg cag gac<br>Ala Thr Gly Gln Thr Gly Leu Pro Gly Asp Ser Gly Leu Leu Gln Asp<br>335                      340                      345                    350 | 1299 |
| tcc tct cta cct ccc att cca agg acc aat gag gac caa agg gag cca<br>Ser Ser Leu Pro Pro Ile Pro Arg Thr Asn Glu Asp Gln Arg Glu Pro<br>                    355                      360                    365 | 1347 |
| atc ttg tcc act gct aag aaa acc aag ccc cat ccc aga tct gga gac<br>Ile Leu Ser Thr Ala Lys Lys Thr Lys Pro His Pro Arg Ser Gly Asp<br>           370                      375                    380 | 1395 |
| ccc tca gcc cct cct cgg ctg gcc ctg agc tct gcc ctc cct ggg ccc<br>Pro Ser Ala Pro Pro Arg Leu Ala Leu Ser Ser Ala Leu Pro Gly Pro<br>385                      390                      395 | 1443 |
| cct ctg ccc gct cgg ggg cat gca ctg ctg cgc tgg acc gca ctg ctg<br>Pro Leu Pro Ala Arg Gly His Ala Leu Leu Arg Trp Thr Ala Leu Leu | 1491 |

-continued

```
                400               405              410
      tgc ctg atg gtc ttt gtc agt gcc ttc tcc ttt ggg ttt ggg cca gtg       1539
      Cys Leu Met Val Phe Val Ser Ala Phe Ser Phe Gly Phe Gly Pro Val
      415                 420                 425                 430 acc tgg ctt gtc ctc agc gag atc tac cct gtg gag ata cga gga aga       1587
      Thr Trp Leu Val Leu Ser Glu Ile Tyr Pro Val Glu Ile Arg Gly Arg
                      435                 440                 445 gcc ttc gcc ttc tgc aac agc ttc aac tgg gcg gcc aac ctc ttc atc       1635
      Ala Phe Ala Phe Cys Asn Ser Phe Asn Trp Ala Ala Asn Leu Phe Ile
                  450                 455                 460 agc ctc tcc ttc ctc gat ctc att ggc acc atc ggc ttg tcc tgg acc       1683
      Ser Leu Ser Phe Leu Asp Leu Ile Gly Thr Ile Gly Leu Ser Trp Thr
              465                 470                 475 ttc ctg ctc tac gga ctg acc gct gtc ctc ggc ctg ggc ttc atc tat       1731
      Phe Leu Leu Tyr Gly Leu Thr Ala Val Leu Gly Leu Gly Phe Ile Tyr
          480                 485                 490 tta ttt gtt cct gaa aca aaa ggc cag tcg ttg gca gag ata gac cag       1779
      Leu Phe Val Pro Glu Thr Lys Gly Gln Ser Leu Ala Glu Ile Asp Gln
      495                 500                 505                 510 cag ttc cag aag aga cgg ttc acc ctg agc ttt ggc cac agg cag aac       1827
      Gln Phe Gln Lys Arg Arg Phe Thr Leu Ser Phe Gly His Arg Gln Asn
                      515                 520                 525 tcc act ggc atc ccg tac agc cgc atc gag atc tct gcg gcc tcc tga       1875
      Ser Thr Gly Ile Pro Tyr Ser Arg Ile Glu Ile Ser Ala Ala Ser
                  530                 535                 540 ggaatccgtc tgcctggaat tctgaactg tggctttggc agaccatctc cagcatcctg      1935
cttcctaggc cccagagcac aagttccagc tggtcttttg ggagtggccc ctgcccccaa     1995
aggtggtttg cttttgctgg ggtaaaaagg atgaaagttt gagaatgccc aattcttcat     2055
tttgggtttc aggccctgaa ggttcttgag gatctagttt catgcctcgg tttccccatt     2115
gacttggaca ttttttgcagt ttttataaga agaatattct atgaagtctt tgttgcccca    2175 tggattttt tcaaagaatc tcaggggtac caatccgggc aggaggtttt tcccgatatc      2235
acccctaaat ccaaatgagg atatcatctt ttctaatctc ttttttcaac tggctgggac     2295
attttcggaa gggggaagtc tcttttttta ctcttatcat tttttttttt tgaggtggag     2355
tctcattctg ttgcccaggc tggcctgatc ttggctcact gcaacctcca cttcctgggt     2415
tcaagcgatt ctcctgcctc agcctcctaa gtagctggga ttacaggcgc gtgccaccac     2475
acccagctaa tttatttta gcagagatgg ggtttcactg tgttggccag gctggtcgtg      2535
aactcctgag ctcaagtgat ccacccacct cagcctccca gagtgctagg attacaggcc     2595
ttttgactct tttatctgag ttttattgac ccctctaatt ctcttaccca gaatatttat     2655
ccttcaccag caactctgac tctttgacgg gaggcctcag ttctagtcct tggtctgctg     2715
gtgtcattgc tgtaggaatg accacgggcc tcagtttccc catttgtata atgggaagcc     2775
tgtaccaggt cattcttaag atttctcctg actccagtga gctggaattc taaatgctgg     2835
tctaggagct gtctccagga tggtgcagga tggctttgcg gaaaggagat gggtttggag     2895
gccaacaaac ctgcttgtca atattgcctt tgcctcttgg cagcccttga acttgagtaa     2955
ataacaactc cctgaacctc agtttcctca tctgcagaat ggggataatt atgtcccagg     3015
ggtatattta gaccctgttt cctttcagga gggtccccag ctggtccagg cctgggaaa      3075 tttctactta tcctcattac ccaggtccct cctttggacc ctgtaaaggg tcagggtgaa     3135
tcagatgggg gactgagcaa gtagctatga ctgcagatca tgtaaggaag ggactgacaa     3195
gaagctccca gatgctgggg agaatgaaga gctaaaatag atcctaggtg ctggatgctt     3255
```

-continued

```
tgtcatccat gcgtgcacat atgggtgctg gcagagcccc caaggactct ggcctctcga      3315
gttctcctat cttctccatt ctagatgctt cccttgtatc cagtgatgtg ctggagctgg      3375 cttttgccaag cttgtgagag ctggttgcta cattttcagg attttttacaa gttggtaaac    3435 acagccatta taaaaaatta aatgatttaa atttataatt aagtaaatta cattaaaaca      3495
aaaaaattat actcaaaatt cattacttaa ttttactacc tgttactatt atctgtgctt      3555
ttgaggctat ttctacatag taactcttat ggagacctag gggagacacc gcgcatctct      3615
tcctgattcc ccactcaatg acatcatgtt agtctttggt tgcttaactg gctgtgggga      3675
gtgtttttgt atcacaaaga ttagagagga ctacacatca gggcttgatt tattgtttgt      3735
tgattttcta gacttcagaa catgctggat aaaatgtcag taatgcaaat taaactttaa      3795
agtatgtctt gtttgtagcc aatacatggt gtatagcacc aaaaaatgga gggattattc      3855
ttccagtagt tgaacactgt catccgtttc agctgacagc tgctcaaatc atttaagaag      3915
gagttctgac attcattttc attgttttac ttttgtcttc ctcactagtg taaacaaaaa      3975
tttcaaccag cattcatgcc gaacctatac ccattcttca gtgcctagct gtacagttat      4035
cagggatttt tattcgtagt ctaattttgt caaatcatgg ccaaatcgca gtgatagttg      4095
actttggata caaggtttgg caaaaaaaaa aatattaaca aaatattctg taagaatcaa      4155
ttggctatat ggaatttagg ataaagaata tttacaataa agaatattta caataaagag      4215
tttattatta tttgtaagtt gtgtgcaaca aacataccct ttatctctgt aaaatttata      4275
cacacaaaaa ttaacaaaag attctgtaag aattaattgg ctatatggaa tttaggatag      4335
aatatttaca ataaagagta tttacaataa agagtttgtt attatttgta aaaaaaaaa       4395
```

<210> SEQ ID NO 2
<211> LENGTH: 541
<212> TYPE: PRT
<213> ORGANISM: Homo sapiens

<400> SEQUENCE: 2

```
Met Gly His Ser Pro Val Leu Pro Leu Cys Ala Ser Val Ser Leu
1               5                   10                  15

Leu Gly Gly Leu Thr Phe Gly Tyr Glu Leu Ala Val Ile Ser Gly Ala
                20                  25                  30

Leu Leu Pro Leu Gln Leu Asp Phe Gly Leu Ser Cys Leu Glu Gln Glu
            35                  40                  45

Phe Leu Val Gly Ser Leu Leu Gly Ala Leu Leu Ala Ser Leu Val
    50                  55                  60

Gly Gly Phe Leu Ile Asp Cys Tyr Gly Arg Lys Gln Ala Ile Leu Gly
65                  70                  75                  80

Ser Asn Leu Val Leu Leu Ala Gly Ser Leu Thr Leu Gly Leu Ala Gly
                85                  90                  95

Ser Leu Ala Trp Leu Val Leu Gly Arg Ala Val Gly Phe Ala Ile
            100                 105                 110

Ser Leu Ser Ser Met Ala Cys Cys Ile Tyr Val Ser Glu Leu Val Gly
        115                 120                 125

Pro Arg Gln Arg Gly Val Leu Val Ser Leu Tyr Glu Ala Gly Ile Thr
    130                 135                 140

Val Gly Ile Leu Leu Ser Tyr Ala Leu Asn Tyr Ala Leu Ala Gly Thr
145                 150                 155                 160

Pro Trp Gly Trp Arg His Met Phe Gly Trp Ala Thr Ala Pro Ala Val
                165                 170                 175
```

```
Leu Gln Ser Leu Ser Leu Leu Phe Leu Pro Ala Gly Thr Asp Glu Thr
            180                 185                 190

Ala Thr His Lys Asp Leu Ile Pro Leu Gln Gly Gly Glu Ala Pro Lys
        195                 200                 205

Leu Gly Pro Gly Arg Pro Arg Tyr Ser Phe Leu Asp Leu Phe Arg Ala
    210                 215                 220

Arg Asp Asn Met Arg Gly Arg Thr Thr Val Gly Leu Gly Leu Val Leu
225                 230                 235                 240

Phe Gln Gln Leu Thr Gly Gln Pro Asn Val Leu Cys Tyr Ala Ser Thr
                245                 250                 255

Ile Phe Ser Ser Val Gly Phe His Gly Gly Ser Ser Ala Val Leu Ala
            260                 265                 270

Ser Val Gly Leu Gly Ala Val Lys Val Ala Ala Thr Leu Thr Ala Met
        275                 280                 285

Gly Leu Val Asp Arg Ala Gly Arg Arg Ala Leu Leu Leu Ala Gly Cys
    290                 295                 300

Ala Leu Met Ala Leu Ser Val Ser Gly Ile Gly Leu Val Ser Phe Ala
305                 310                 315                 320

Val Pro Met Asp Ser Gly Pro Ser Cys Leu Ala Val Pro Asn Ala Thr
                325                 330                 335

Gly Gln Thr Gly Leu Pro Gly Asp Ser Gly Leu Leu Gln Asp Ser Ser
            340                 345                 350

Leu Pro Pro Ile Pro Arg Thr Asn Glu Asp Gln Arg Glu Pro Ile Leu
        355                 360                 365

Ser Thr Ala Lys Lys Thr Lys Pro His Pro Arg Ser Gly Asp Pro Ser
    370                 375                 380

Ala Pro Pro Arg Leu Ala Leu Ser Ser Ala Leu Pro Gly Pro Pro Leu
385                 390                 395                 400

Pro Ala Arg Gly His Ala Leu Leu Arg Trp Thr Ala Leu Leu Cys Leu
                405                 410                 415

Met Val Phe Val Ser Ala Phe Ser Phe Gly Phe Gly Pro Val Thr Trp
            420                 425                 430

Leu Val Leu Ser Glu Ile Tyr Pro Val Glu Ile Arg Gly Arg Ala Phe
        435                 440                 445

Ala Phe Cys Asn Ser Phe Asn Trp Ala Ala Asn Leu Phe Ile Ser Leu
    450                 455                 460

Ser Phe Leu Asp Leu Ile Gly Thr Ile Gly Leu Ser Trp Thr Phe Leu
465                 470                 475                 480

Leu Tyr Gly Leu Thr Ala Val Leu Gly Leu Gly Phe Ile Tyr Leu Phe
                485                 490                 495

Val Pro Glu Thr Lys Gly Gln Ser Leu Ala Glu Ile Asp Gln Gln Phe
            500                 505                 510

Gln Lys Arg Arg Phe Thr Leu Ser Phe Gly His Arg Gln Asn Ser Thr
        515                 520                 525

Gly Ile Pro Tyr Ser Arg Ile Glu Ile Ser Ala Ala Ser
    530                 535                 540

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
```
ggcacctctt ccctgcaaag                                               20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
ccctcccgcg cgcagcgccg                                               20

<210> SEQ ID NO 5
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 5
cgtcccgcct ccaggcct                                                 18

<210> SEQ ID NO 6
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 6
ccatggcgag cgggact                                                  17

<210> SEQ ID NO 7
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 7
cgtcccgcct ccaggcct                                                 18

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8
ggcggtgtct acaccctgg                                                19

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 9
tgacagatgg agggaaggtt g                                             21

<210> SEQ ID NO 10
<211> LENGTH: 19
<212> TYPE: DNA

```
<213> ORGANISM: Artificial sequence
<220> FEATURE:
<223> OTHER INFORMATION: Synthetic oligonucleotide

<400> SEQUENCE: 10
aggagcaggc tgcccacca                                                  19

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ctggcagtca tatcaggtgc                                                 20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
aatggcgaag ccaaccacag                                                 20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
ggagcaactt ggtgctgctg                                                 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
agtggcccag ccgaacatgt                                                 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
ctcaactatg cactggctgg                                                 20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
cggagctgaa gatggtggag                                                 20
```

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
ctcttccagc aactaacagg g                                          21

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
agcttgggcc tgagtccatg                                            20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
agtggcatag gcctcgtcag                                            20

<210> SEQ ID NO 20
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 20
agaagtctcc agagtcacct g                                          21

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
ggctgcatgt ttgacctgat g                                          21

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 22
gctttagagt agggagcttg g                                          21

<210> SEQ ID NO 23
<211> LENGTH: 21
<212> TYPE: DNA
<213> ORGANISM: Artificial sequence
<220> FEATURE:

```
<223> OTHER INFORMATION: Synthetic oligonucleotide

<400> SEQUENCE: 23
tgacctagaa cctaccagtt g                                              21

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
tcctgaagct gtgtgcttgg                                                20

<210> SEQ ID NO 25
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 25
gggaacccca gtggaaggt                                                 19

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
caggcagacg gattcctcag                                                20

<210> SEQ ID NO 27
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 27
aactccactg gcatcccgt                                                 19

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
catgaaacta gatcctcaag                                                20

<210> SEQ ID NO 29
<211> LENGTH: 16
<212> TYPE: DNA
<213> ORGANISM: Homo sapiens
<220> FEATURE:
<221> NAME/KEY: misc_feature
<223> OTHER INFORMATION: Exon 1 5' splice donor

<400> SEQUENCE: 29
tcgccatggg taagtc                                                    16
```

```
<210> SEQ ID NO 30
<211> LENGTH: 15
<212> TYPE: DNA
<213> ORGANISM: Homo sapiens
<220> FEATURE:
<221> NAME/KEY: misc_feature
<223> OTHER INFORMATION: Exon 2 3' splice acceptor

<400> SEQUENCE: 30
tttttaggcc actcc                                                    15

<210> SEQ ID NO 31
<211> LENGTH: 14
<212> TYPE: DNA
<213> ORGANISM: Homo sapiens
<220> FEATURE:
<221> NAME/KEY: misc_feature
<223> OTHER INFORMATION: Exon 2 5' splice acceptor

<400> SEQUENCE: 31
gggccaggta agtg                                                     14

<210> SEQ ID NO 32
<211> LENGTH: 15
<212> TYPE: DNA
<213> ORGANISM: Homo sapiens
<220> FEATURE:
<221> NAME/KEY: misc_feature
<223> OTHER INFORMATION: Exon 3 3' splice acceptor

<400> SEQUENCE: 32
accctagtga cctgg                                                    15

<210> SEQ ID NO 33
<211> LENGTH: 14
<212> TYPE: DNA
<213> ORGANISM: Homo sapiens
<220> FEATURE:
<221> NAME/KEY: misc_feature
<223> OTHER INFORMATION: Exon 3 5' splice donor

<400> SEQUENCE: 33
ctcattggtg agtc                                                     14

<210> SEQ ID NO 34
<211> LENGTH: 15
<212> TYPE: DNA
<213> ORGANISM: Homo sapiens
<220> FEATURE:
<221> NAME/KEY: misc_feature
<223> OTHER INFORMATION: Exon 4 3' splice acceptor

<400> SEQUENCE: 34
tttccaggca ccatc                                                    15

<210> SEQ ID NO 35
<211> LENGTH: 15
<212> TYPE: DNA
<213> ORGANISM: Homo sapiens
<220> FEATURE:
<221> NAME/KEY: misc_feature
<223> OTHER INFORMATION: Exon 4 5' splice donor

<400> SEQUENCE: 35
aagagacggt aggaa                                                    15
```

```
<210> SEQ ID NO 36
<211> LENGTH: 14
<212> TYPE: DNA
<213> ORGANISM: Homo sapiens
<220> FEATURE:
<221> NAME/KEY: misc_feature
<223> OTHER INFORMATION: Exon 5 3' splice acceptor

<400> SEQUENCE: 36
ctgacaggtt cacc                                                       14

<210> SEQ ID NO 37
<211> LENGTH: 26
<212> TYPE: DNA
<213> ORGANISM: Homo sapiens
<220> FEATURE:
<221> NAME/KEY: 3'UTR
<222> LOCATION: (1)..(26)
<220> FEATURE:
<221> NAME/KEY: polyA_site
<222> LOCATION: (26)..(26)

<400> SEQUENCE: 37
aataaagagt tgttattaa tttgta                                           26

<210> SEQ ID NO 38
<211> LENGTH: 492
<212> TYPE: PRT
<213> ORGANISM: Homo sapiens

<400> SEQUENCE: 38
```

Met Glu Pro Ser Ser Lys Lys Leu Thr Gly Arg Leu Met Leu Ala Val
1               5                   10                  15

Gly Gly Ala Val Leu Gly Ser Leu Gln Phe Gly Tyr Asn Thr Gly Val
            20                  25                  30

Ile Asn Ala Pro Gln Lys Val Ile Glu Glu Phe Tyr Asn Gln Thr Trp
        35                  40                  45

Val His Arg Tyr Gly Glu Ser Ile Leu Pro Thr Thr Leu Thr Thr Leu
    50                  55                  60

Trp Ser Leu Ser Val Ala Ile Phe Ser Val Gly Gly Met Ile Gly Ser
65                  70                  75                  80

Phe Ser Val Gly Leu Phe Val Asn Arg Phe Gly Arg Arg Asn Ser Met
                85                  90                  95

Leu Met Met Asn Leu Leu Ala Phe Val Ser Ala Val Leu Met Gly Phe
            100                 105                 110

Ser Lys Leu Gly Lys Ser Phe Glu Met Leu Ile Leu Gly Arg Phe Ile
        115                 120                 125

Ile Gly Val Tyr Cys Gly Leu Thr Thr Gly Phe Val Pro Met Tyr Val
    130                 135                 140

Gly Glu Val Ser Pro Thr Ala Phe Arg Gly Ala Leu Gly Thr Leu His
145                 150                 155                 160

Gln Leu Gly Ile Val Val Gly Ile Leu Ile Ala Gln Val Phe Gly Leu
                165                 170                 175

Asp Ser Ile Met Gly Asn Lys Asp Leu Trp Pro Leu Leu Leu Ser Ile
            180                 185                 190

Ile Phe Ile Pro Ala Leu Leu Gln Cys Ile Val Leu Pro Phe Cys Pro
        195                 200                 205

Glu Ser Pro Arg Phe Leu Leu Ile Asn Arg Asn Glu Glu Asn Arg Ala
    210                 215                 220

Lys Ser Val Leu Lys Lys Leu Arg Gly Thr Ala Asp Val Thr His Asp

-continued

```
225                 230                 235                 240

Leu Gln Glu Met Lys Glu Glu Ser Arg Gln Met Met Arg Glu Lys Lys
                245                 250                 255

Val Thr Ile Leu Glu Leu Phe Arg Ser Pro Ala Tyr Arg Gln Pro Ile
                260                 265                 270

Leu Ile Ala Val Val Leu Gln Leu Ser Gln Gln Leu Ser Gly Ile Asn
                275                 280                 285

Ala Val Phe Tyr Tyr Ser Thr Ser Ile Phe Glu Lys Ala Gly Val Gln
                290                 295                 300

Gln Pro Val Tyr Ala Thr Ile Gly Ser Gly Ile Val Asn Thr Ala Phe
305                 310                 315                 320

Thr Val Val Ser Leu Phe Val Val Glu Arg Ala Gly Arg Arg Thr Leu
                325                 330                 335

His Leu Ile Gly Leu Ala Gly Met Ala Gly Cys Ala Ile Leu Met Thr
                340                 345                 350

Ile Ala Leu Ala Leu Leu Glu Gln Leu Pro Trp Met Ser Tyr Leu Ser
                355                 360                 365

Ile Val Ala Ile Phe Gly Phe Val Ala Phe Phe Glu Val Gly Pro Gly
                370                 375                 380

Pro Ile Pro Trp Phe Ile Val Ala Glu Leu Phe Ser Gln Gly Pro Arg
385                 390                 395                 400

Pro Ala Ala Ile Ala Val Ala Gly Phe Ser Asn Trp Thr Ser Asn Phe
                405                 410                 415

Ile Val Gly Met Cys Phe Gln Tyr Val Glu Gln Leu Cys Gly Pro Tyr
                420                 425                 430

Val Phe Ile Ile Phe Thr Val Leu Leu Val Leu Phe Phe Ile Phe Thr
                435                 440                 445

Tyr Phe Lys Val Pro Glu Thr Lys Gly Arg Thr Phe Asp Glu Ile Ala
                450                 455                 460

Ser Gly Phe Arg Gln Gly Gly Ala Ser Gln Ser Asp Lys Thr Pro Glu
465                 470                 475                 480

Glu Leu Phe His Pro Leu Gly Ala Asp Ser Gln Val
                485                 490

<210> SEQ ID NO 39
<211> LENGTH: 524
<212> TYPE: PRT
<213> ORGANISM: Homo sapiens

<400> SEQUENCE: 39

Met Thr Glu Asp Lys Val Thr Gly Thr Leu Val Phe Thr Val Ile Thr
1               5                   10                  15

Ala Val Leu Gly Ser Phe Gln Phe Gly Tyr Asp Ile Gly Val Ile Asn
                20                  25                  30

Ala Pro Gln Gln Val Ile Ile Ser His Tyr Arg His Val Leu Gly Val
                35                  40                  45

Pro Leu Asp Asp Arg Lys Ala Ile Asn Asn Tyr Val Ile Asn Ser Thr
50                  55                  60

Asp Glu Leu Pro Thr Ile Ser Tyr Ser Met Asn Pro Lys Pro Thr Pro
65                  70                  75                  80

Trp Ala Glu Glu Glu Thr Val Ala Ala Gln Leu Ile Thr Met Leu
                85                  90                  95

Trp Ser Leu Ser Val Ser Ser Phe Ala Val Gly Gly Met Thr Ala Ser
                100                 105                 110
```

-continued

```
Phe Phe Gly Gly Trp Leu Gly Asp Thr Leu Gly Arg Ile Lys Ala Met
        115                 120                 125

Leu Val Ala Asn Ile Leu Ser Leu Val Gly Ala Leu Leu Met Gly Phe
        130                 135                 140

Ser Lys Leu Gly Pro Ser His Ile Leu Ile Ala Gly Arg Ser Ile
145                 150                 155                 160

Ser Gly Leu Tyr Cys Gly Leu Ile Ser Gly Leu Val Pro Met Tyr Ile
                165                 170                 175

Gly Glu Ile Ala Pro Thr Ala Leu Arg Gly Ala Leu Gly Thr Phe His
                180                 185                 190

Gln Leu Ala Ile Val Thr Gly Ile Leu Ile Ser Gln Ile Ile Gly Leu
        195                 200                 205

Glu Phe Ile Leu Gly Asn Tyr Asp Leu Trp His Ile Leu Leu Gly Leu
        210                 215                 220

Ser Gly Val Arg Ala Ile Leu Gln Ser Leu Leu Leu Phe Phe Cys Pro
225                 230                 235                 240

Glu Ser Pro Arg Tyr Leu Tyr Ile Lys Leu Asp Glu Val Lys Ala
                245                 250                 255

Lys Gln Ser Leu Lys Arg Leu Arg Gly Tyr Asp Asp Val Thr Lys Asp
                260                 265                 270

Ile Asn Glu Met Arg Lys Glu Arg Glu Glu Ala Ser Ser Glu Gln Lys
        275                 280                 285

Val Ser Ile Ile Gln Leu Phe Thr Asn Ser Ser Tyr Arg Gln Pro Ile
        290                 295                 300

Leu Val Ala Leu Met Leu His Val Ala Gln Gln Phe Ser Gly Ile Asn
305                 310                 315                 320

Gly Ile Phe Tyr Tyr Ser Thr Ser Ile Phe Gln Thr Ala Gly Ile Ser
                325                 330                 335

Lys Pro Val Tyr Ala Thr Ile Gly Val Gly Ala Val Asn Met Val Phe
                340                 345                 350

Thr Ala Val Ser Val Phe Leu Val Glu Lys Ala Gly Arg Arg Ser Leu
        355                 360                 365

Phe Leu Ile Gly Met Ser Gly Met Phe Val Cys Ala Ile Phe Met Ser
        370                 375                 380

Val Gly Leu Val Leu Leu Asn Lys Phe Ser Trp Met Ser Tyr Val Ser
385                 390                 395                 400

Met Ile Ala Ile Phe Leu Phe Val Ser Phe Phe Glu Ile Gly Pro Gly
                405                 410                 415

Pro Ile Pro Trp Phe Met Val Ala Glu Phe Phe Ser Gln Gly Pro Arg
                420                 425                 430

Pro Ala Ala Leu Ala Ile Ala Ala Phe Ser Asn Trp Thr Cys Asn Phe
        435                 440                 445

Ile Val Ala Leu Cys Phe Gln Tyr Ile Ala Asp Phe Cys Gly Pro Tyr
        450                 455                 460

Val Phe Phe Leu Phe Ala Gly Val Leu Leu Ala Phe Thr Leu Phe Thr
465                 470                 475                 480

Phe Phe Lys Val Pro Glu Thr Lys Gly Lys Ser Phe Glu Glu Ile Ala
                485                 490                 495

Ala Glu Phe Gln Lys Lys Ser Gly Ser Ala His Arg Pro Lys Ala Ala
                500                 505                 510

Val Glu Met Lys Phe Leu Gly Ala Thr Glu Thr Val
        515                 520
```

```
<210> SEQ ID NO 40
<211> LENGTH: 496
<212> TYPE: PRT
<213> ORGANISM: Homo sapiens

<400> SEQUENCE: 40
```

| | | | | | | | | | | | | | | | |
|---|---|---|---|---|---|---|---|---|---|---|---|---|---|---|---|
| Met | Gly | Thr | Gln | Lys | Val | Thr | Pro | Ala | Leu | Ile | Phe | Ala | Ile | Thr | Val |
| 1 | | | | 5 | | | | | 10 | | | | | 15 | |
| Ala | Thr | Ile | Gly | Ser | Phe | Gln | Phe | Gly | Tyr | Asn | Thr | Gly | Val | Ile | Asn |
| | | | 20 | | | | | 25 | | | | | 30 | | |
| Ala | Pro | Glu | Lys | Ile | Ile | Lys | Glu | Phe | Ile | Asn | Lys | Thr | Leu | Thr | Asp |
| | | | | 35 | | | | | 40 | | | | | 45 | |
| Lys | Gly | Asn | Ala | Pro | Pro | Ser | Glu | Val | Leu | Leu | Thr | Ser | Leu | Trp | Ser |
| | 50 | | | | | 55 | | | | | 60 | | | | |
| Leu | Ser | Val | Ala | Ile | Phe | Ser | Val | Gly | Gly | Met | Ile | Gly | Ser | Phe | Ser |
| 65 | | | | | 70 | | | | | 75 | | | | | 80 |
| Val | Gly | Leu | Phe | Val | Asn | Arg | Phe | Gly | Arg | Arg | Asn | Ser | Met | Leu | Ile |
| | | | | 85 | | | | | 90 | | | | | 95 | |
| Val | Asn | Leu | Leu | Ala | Val | Thr | Gly | Gly | Cys | Phe | Met | Gly | Leu | Cys | Lys |
| | | | 100 | | | | | 105 | | | | | 110 | | |
| Val | Ala | Lys | Ser | Val | Glu | Met | Leu | Ile | Leu | Gly | Arg | Leu | Val | Ile | Gly |
| | | | | 115 | | | | | 120 | | | | | 125 | |
| Leu | Phe | Cys | Gly | Leu | Cys | Thr | Gly | Phe | Val | Pro | Met | Tyr | Ile | Gly | Glu |
| | 130 | | | | | 135 | | | | | 140 | | | | |
| Ile | Ser | Pro | Thr | Ala | Leu | Arg | Gly | Ala | Phe | Gly | Thr | Leu | Asn | Gln | Leu |
| 145 | | | | | 150 | | | | | 155 | | | | | 160 |
| Gly | Ile | Val | Val | Gly | Ile | Leu | Val | Ala | Gln | Ile | Phe | Gly | Leu | Glu | Phe |
| | | | | 165 | | | | | 170 | | | | | 175 | |
| Ile | Leu | Gly | Ser | Glu | Glu | Leu | Trp | Pro | Leu | Leu | Leu | Gly | Phe | Thr | Ile |
| | | | 180 | | | | | 185 | | | | | 190 | | |
| Leu | Pro | Ala | Ile | Leu | Gln | Ser | Ala | Ala | Leu | Pro | Phe | Cys | Pro | Glu | Ser |
| | | | | 195 | | | | | 200 | | | | | 205 | |
| Pro | Arg | Phe | Leu | Leu | Ile | Asn | Arg | Lys | Glu | Glu | Asn | Ala | Lys | Gln |
| | 210 | | | | | 215 | | | | | 220 | | | | |
| Ile | Leu | Gln | Arg | Leu | Trp | Gly | Thr | Gln | Asp | Val | Ser | Gln | Asp | Ile | Gln |
| 225 | | | | | 230 | | | | | 235 | | | | | 240 |
| Glu | Met | Lys | Asp | Glu | Ser | Ala | Arg | Met | Ser | Gln | Glu | Lys | Gln | Val | Thr |
| | | | | 245 | | | | | 250 | | | | | 255 | |
| Val | Leu | Glu | Leu | Phe | Arg | Val | Ser | Ser | Tyr | Arg | Gln | Pro | Ile | Ile | Ile |
| | | | 260 | | | | | 265 | | | | | 270 | | |
| Ser | Ile | Val | Leu | Gln | Leu | Ser | Gln | Gln | Leu | Ser | Gly | Ile | Asn | Ala | Val |
| | | | | 275 | | | | | 280 | | | | | 285 | |
| Phe | Tyr | Tyr | Ser | Thr | Gly | Ile | Phe | Lys | Asp | Ala | Gly | Val | Gln | Glu | Pro |
| | 290 | | | | | 295 | | | | | 300 | | | | |
| Ile | Tyr | Ala | Thr | Ile | Gly | Ala | Gly | Val | Val | Asn | Thr | Ile | Phe | Thr | Val |
| 305 | | | | | 310 | | | | | 315 | | | | | 320 |
| Val | Ser | Leu | Phe | Leu | Val | Glu | Arg | Ala | Gly | Arg | Arg | Thr | Leu | His | Met |
| | | | | 325 | | | | | 330 | | | | | 335 | |
| Ile | Gly | Leu | Gly | Gly | Met | Ala | Phe | Cys | Ser | Thr | Leu | Met | Thr | Val | Ser |
| | | | 340 | | | | | 345 | | | | | 350 | | |
| Leu | Leu | Leu | Lys | Asp | Asn | Tyr | Asn | Gly | Met | Ser | Phe | Val | Cys | Ile | Gly |
| | | | | 355 | | | | | 360 | | | | | 365 | |
| Ala | Ile | Leu | Val | Phe | Val | Ala | Phe | Phe | Glu | Ile | Gly | Pro | Gly | Pro | Ile |
| | 370 | | | | | 375 | | | | | 380 | | | | |

```
Pro Trp Phe Ile Val Ala Glu Leu Phe Ser Gln Gly Pro Arg Pro Ala
385                 390                 395                 400

Ala Met Ala Val Ala Gly Cys Ser Asn Trp Thr Ser Asn Phe Leu Val
                405                 410                 415

Gly Leu Leu Phe Pro Ser Ala Ala His Tyr Leu Gly Ala Tyr Val Phe
            420                 425                 430

Ile Ile Phe Thr Gly Phe Leu Ile Thr Phe Leu Ala Phe Thr Phe Phe
        435                 440                 445

Lys Val Pro Glu Thr Arg Gly Arg Thr Phe Glu Asp Ile Thr Arg Ala
    450                 455                 460

Phe Glu Gly Gln Ala His Gly Ala Asp Arg Ser Gly Lys Asp Gly Val
465                 470                 475                 480

Met Glu Met Asn Ser Ile Glu Pro Ala Lys Glu Thr Thr Asn Val
                485                 490                 495

<210> SEQ ID NO 41
<211> LENGTH: 509
<212> TYPE: PRT
<213> ORGANISM: Homo sapiens

<400> SEQUENCE: 41

Met Pro Ser Gly Phe Gln Gln Ile Gly Ser Glu Asp Gly Glu Pro Pro
1               5                   10                  15

Gln Gln Arg Val Thr Gly Thr Leu Val Leu Ala Val Phe Ser Ala Val
                20                  25                  30

Leu Gly Ser Leu Gln Phe Gly Tyr Asn Ile Gly Val Ile Asn Ala Pro
            35                  40                  45

Gln Lys Val Ile Glu Gln Ser Tyr Asn Glu Thr Trp Leu Gly Arg Gln
50                  55                  60

Gly Pro Glu Gly Pro Ser Ser Ile Pro Pro Gly Thr Leu Thr Thr Leu
65                  70                  75                  80

Trp Ala Leu Ser Val Ala Ile Phe Ser Val Gly Gly Met Ile Ser Ser
                85                  90                  95

Phe Leu Ile Gly Ile Ile Ser Gln Trp Leu Gly Arg Lys Arg Ala Met
            100                 105                 110

Leu Val Asn Asn Val Leu Ala Val Leu Gly Gly Ser Leu Met Gly Leu
        115                 120                 125

Ala Asn Ala Ala Ala Ser Tyr Glu Met Leu Ile Leu Gly Arg Phe Leu
130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Ile Gly Ile Leu Ile Ala Gln Val Leu Gly Leu
            180                 185                 190

Glu Ser Leu Leu Gly Thr Ala Ser Leu Trp Pro Leu Leu Leu Gly Leu
        195                 200                 205

Thr Val Leu Pro Ala Leu Leu Gln Leu Val Leu Leu Pro Phe Cys Pro
210                 215                 220

Glu Ser Pro Arg Tyr Leu Tyr Ile Ile Gln Asn Leu Glu Gly Pro Ala
225                 230                 235                 240

Arg Lys Ser Leu Lys Arg Leu Thr Gly Trp Ala Asp Val Ser Gly Val
                245                 250                 255

Leu Ala Glu Leu Lys Asp Glu Lys Arg Lys Leu Glu Arg Glu Arg Pro
            260                 265                 270
```

-continued

Leu Ser Leu Leu Gln Leu Leu Gly Ser Arg Thr His Arg Gln Pro Leu
        275                 280                 285

Ile Ile Ala Val Val Leu Gln Leu Ser Gln Gln Leu Ser Gly Ile Asn
    290                 295                 300

Ala Val Phe Tyr Tyr Ser Thr Ser Ile Phe Glu Thr Ala Gly Val Gly
305                 310                 315                 320

Gln Pro Ala Tyr Ala Thr Ile Gly Ala Gly Val Val Asn Thr Val Phe
                325                 330                 335

Thr Leu Val Ser Val Leu Leu Val Glu Arg Ala Gly Arg Arg Thr Leu
            340                 345                 350

His Leu Leu Gly Leu Ala Gly Met Cys Gly Cys Ala Ile Leu Met Thr
        355                 360                 365

Val Ala Leu Leu Leu Leu Glu Arg Val Pro Ala Met Ser Tyr Val Ser
    370                 375                 380

Ile Val Ala Ile Phe Gly Phe Val Ala Phe Glu Ile Gly Pro Gly
385                 390                 395                 400

Pro Ile Pro Trp Phe Ile Val Ala Glu Leu Phe Ser Gln Gly Pro Arg
                405                 410                 415

Pro Ala Ala Met Ala Val Ala Gly Phe Ser Asn Trp Thr Ser Asn Phe
            420                 425                 430

Ile Ile Gly Met Gly Phe Gln Tyr Val Ala Glu Ala Met Gly Pro Tyr
        435                 440                 445

Val Phe Leu Leu Phe Ala Val Leu Leu Gly Phe Phe Ile Phe Thr
    450                 455                 460

Phe Leu Arg Val Pro Glu Thr Arg Gly Arg Thr Phe Asp Gln Ile Ser
465                 470                 475                 480

Ala Ala Phe His Arg Thr Pro Ser Leu Leu Glu Gln Glu Val Lys Pro
                485                 490                 495

Ser Thr Glu Leu Glu Tyr Leu Gly Pro Asp Glu Asn Asp
            500                 505

<210> SEQ ID NO 42
<211> LENGTH: 501
<212> TYPE: PRT
<213> ORGANISM: Homo sapiens

<400> SEQUENCE: 42

Met Glu Gln Gln Asp Gln Ser Met Lys Glu Gly Arg Leu Thr Leu Val
1               5                   10                  15

Leu Ala Leu Ala Thr Leu Ile Ala Ala Phe Gly Ser Ser Phe Gln Tyr
            20                  25                  30

Gly Tyr Asn Val Ala Ala Val Asn Ser Pro Ala Leu Leu Met Gln Gln
        35                  40                  45

Phe Tyr Asn Glu Thr Tyr Tyr Gly Arg Thr Gly Glu Phe Met Glu Asp
    50                  55                  60

Phe Pro Leu Thr Leu Leu Trp Ser Val Thr Val Ser Met Phe Pro Phe
65                  70                  75                  80

Gly Gly Phe Ile Gly Ser Leu Leu Val Gly Pro Leu Val Asn Lys Phe
                85                  90                  95

Gly Arg Lys Gly Ala Leu Leu Phe Asn Asn Ile Phe Ser Ile Val Pro
            100                 105                 110

Ala Ile Leu Met Gly Cys Ser Arg Val Ala Thr Ser Phe Glu Leu Ile
        115                 120                 125

Ile Ile Ser Arg Leu Leu Val Gly Ile Cys Ala Gly Val Ser Ser Asn

```
                130                 135                 140
Val Val Pro Met Tyr Leu Gly Glu Leu Ala Pro Lys Asn Leu Arg Gly
145                 150                 155                 160

Ala Leu Gly Val Val Pro Gln Leu Phe Ile Thr Val Gly Ile Leu Val
                165                 170                 175

Ala Gln Ile Phe Gly Leu Arg Asn Leu Leu Ala Asn Val Asp Gly Trp
            180                 185                 190

Pro Ile Leu Leu Gly Leu Thr Gly Val Pro Ala Ala Leu Gln Leu Leu
        195                 200                 205

Leu Leu Pro Phe Pro Glu Ser Pro Arg Tyr Leu Leu Ile Gln Lys
    210                 215                 220

Lys Asp Glu Ala Ala Lys Lys Ala Leu Gln Thr Leu Arg Gly Trp
225                 230                 235                 240

Asp Ser Val Asp Arg Glu Val Ala Glu Ile Arg Gln Glu Asp Glu Ala
                245                 250                 255

Glu Lys Ala Ala Gly Phe Ile Ser Val Leu Lys Leu Phe Arg Met Arg
            260                 265                 270

Ser Leu Arg Trp Gln Leu Leu Ser Ile Ile Val Leu Met Gly Gly Gln
        275                 280                 285

Gln Leu Ser Gly Val Asn Ala Ile Tyr Tyr Tyr Ala Asp Gln Ile Tyr
    290                 295                 300

Leu Ser Ala Gly Val Pro Glu Glu His Val Gln Tyr Val Thr Ala Gly
305                 310                 315                 320

Thr Gly Ala Val Asn Val Val Met Thr Phe Cys Ala Val Phe Val Val
                325                 330                 335

Glu Leu Leu Gly Arg Arg Leu Leu Leu Leu Gly Phe Ser Ile Cys
            340                 345                 350

Leu Ile Ala Cys Cys Val Leu Thr Ala Ala Leu Ala Leu Gln Asp Thr
        355                 360                 365

Val Ser Trp Met Pro Tyr Ile Ser Ile Val Cys Val Ile Ser Tyr Val
    370                 375                 380

Ile Gly His Ala Leu Gly Pro Ser Pro Ile Pro Ala Leu Leu Ile Thr
385                 390                 395                 400

Glu Ile Phe Leu Gln Ser Ser Arg Pro Ser Ala Phe Met Val Gly Gly
                405                 410                 415

Ser Val His Trp Leu Ser Asn Phe Thr Val Gly Leu Ile Phe Pro Phe
            420                 425                 430

Ile Gln Glu Gly Leu Gly Pro Tyr Ser Phe Ile Val Phe Ala Val Ile
        435                 440                 445

Cys Leu Leu Thr Thr Ile Tyr Ile Phe Leu Ile Val Pro Glu Thr Lys
    450                 455                 460

Ala Lys Thr Phe Ile Glu Ile Asn Gln Ile Phe Thr Lys Met Asn Lys
465                 470                 475                 480

Val Ser Glu Val Tyr Pro Glu Lys Glu Glu Leu Lys Glu Leu Pro Pro
                485                 490                 495

Val Thr Ser Glu Gln
            500

<210> SEQ ID NO 43
<211> LENGTH: 477
<212> TYPE: PRT
<213> ORGANISM: Homo sapiens

<400> SEQUENCE: 43
```

```
Met Thr Pro Glu Asp Pro Glu Glu Thr Gln Pro Leu Leu Gly Pro Pro
1               5                   10                  15

Gly Gly Ser Ala Pro Arg Gly Arg Arg Val Phe Leu Ala Ala Phe Ala
            20                  25                  30

Ala Ala Leu Gly Pro Leu Ser Phe Gly Phe Ala Leu Gly Tyr Ser Ser
        35                  40                  45

Pro Ala Ile Pro Ser Leu Gln Arg Ala Ala Pro Ala Pro Arg Leu
    50                  55                  60

Asp Asp Ala Ala Ser Trp Phe Gly Ala Val Val Thr Leu Gly Ala
65              70                  75                  80

Ala Ala Gly Gly Val Leu Gly Gly Trp Leu Val Asp Arg Ala Gly Arg
                85                  90                  95

Lys Leu Ser Leu Leu Cys Ser Val Pro Phe Val Ala Gly Phe Ala
            100                 105                 110

Val Ile Thr Ala Ala Gln Asp Val Trp Met Leu Leu Gly Gly Arg Leu
        115                 120                 125

Leu Thr Gly Leu Ala Cys Gly Val Ala Ser Leu Val Ala Pro Val Tyr
    130                 135                 140

Ile Ser Glu Ile Ala Tyr Pro Ala Val Arg Gly Leu Leu Gly Ser Cys
145                 150                 155                 160

Val Gln Leu Met Val Val Gly Ile Leu Leu Ala Tyr Leu Ala Gly
                165                 170                 175

Trp Val Leu Glu Trp Arg Trp Leu Ala Val Leu Gly Cys Val Pro Pro
            180                 185                 190

Ser Leu Met Leu Leu Met Cys Phe Met Pro Glu Thr Pro Arg Phe
            195                 200                 205

Leu Leu Thr Gln His Arg Arg Gln Glu Ala Met Ala Ala Leu Arg Phe
    210                 215                 220

Leu Trp Gly Ser Glu Gln Gly Trp Glu Asp Pro Pro Ile Gly Ala Glu
225                 230                 235                 240

Gln Ser Phe His Leu Ala Leu Leu Arg Gln Pro Gly Ile Tyr Lys Pro
                245                 250                 255

Phe Ile Ile Gly Val Ser Leu Met Ala Phe Gln Gln Leu Ser Gly Val
                260                 265                 270

Asn Ala Val Met Phe Tyr Ala Glu Thr Ile Phe Glu Glu Ala Lys Phe
            275                 280                 285

Lys Asp Ser Ser Leu Ala Ser Val Val Gly Val Ile Gln Val Leu
    290                 295                 300

Phe Thr Ala Val Ala Ala Leu Ile Met Asp Arg Ala Gly Arg Arg Leu
305                 310                 315                 320

Leu Leu Val Leu Ser Gly Val Val Met Val Phe Ser Thr Ser Ala Phe
                325                 330                 335

Gly Ala Tyr Phe Lys Leu Thr Gln Gly Gly Pro Gly Asn Ser Ser His
            340                 345                 350

Val Ala Ile Ser Ala Pro Val Ser Ala Gln Pro Val Asp Ala Ser Val
                355                 360                 365

Gly Leu Ala Trp Leu Ala Val Gly Ser Met Cys Leu Phe Ile Ala Gly
    370                 375                 380

Phe Ala Val Gly Trp Gly Pro Ile Pro Trp Leu Leu Met Ser Glu Ile
385                 390                 395                 400

Phe Pro Leu His Val Lys Gly Val Ala Thr Gly Ile Cys Val Leu Thr
            405                 410                 415

Asn Trp Leu Met Ala Phe Leu Val Thr Lys Glu Phe Ser Ser Leu Met
```

-continued

```
            420                 425                 430
Glu Val Leu Arg Pro Tyr Gly Ala Phe Trp Leu Ala Ser Ala Phe Cys
        435                 440                 445

Ile Phe Ser Val Leu Phe Thr Phe Ser Cys Val Pro Glu Thr Lys Gly
        450                 455                 460

Lys Thr Leu Glu Gln Ile Thr Ala His Phe Glu Gly Arg
465                 470                 475
```